(12) United States Patent
Wang et al.

(10) Patent No.: US 7,517,960 B2
(45) Date of Patent: Apr. 14, 2009

(54) RAT KCNQ5 VOLTAGE-GATED POTASSIUM CHANNEL

(75) Inventors: Qiang Wang, Audubon, PA (US); Thomas Michael Argentieri, Yardley, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/654,326

(22) Filed: Jan. 17, 2007

(65) Prior Publication Data

US 2007/0190553 A1    Aug. 16, 2007

Related U.S. Application Data

(60) Provisional application No. 60/760,249, filed on Jan. 19, 2006.

(51) Int. Cl.
*C07K 14/435* (2006.01)
*C07K 14/705* (2006.01)
*C12P 21/02* (2006.01)
*A61K 38/17* (2006.01)

(52) U.S. Cl. .................... 530/350; 514/2; 514/12; 536/23.5; 435/69.1

(58) Field of Classification Search .............. None
See application file for complete search history.

(56) References Cited

U.S. PATENT DOCUMENTS

| | | | |
|---|---|---|---|
| 5,670,335 | A | 9/1997 | Jan et al. |
| 6,617,131 | B2 * | 9/2003 | Steinmeyer et al. ........ 435/69.1 |
| 6,893,858 | B2 | 5/2005 | Dworetzky et al. |
| 2002/0102677 | A1 | 8/2002 | Jegla |

FOREIGN PATENT DOCUMENTS

| | | |
|---|---|---|
| WO | WO 00/77035 | 12/2000 |
| WO | WO 01/70811 | 9/2001 |
| WO | WO 01/92526 | 12/2001 |
| WO | WO 02/32419 | 4/2002 |

OTHER PUBLICATIONS

Lerche, C. et al., "Molecular Cloning And Functional Expression Of KCNQ5, A Potassium Channel Subunit . . . ", J. Biol. Chem, 275, No. 29, pp. 22395-22400 (2000).
Adams, J. et al., "Voltage-Dependent Potassium Channels: Gating, Ion Permeation And Block", pp. 40-69, Cook, ed. (1990).
Schroeder et al., "KCNQ5, a novel potassium channel . . . ", J. Of Biol. Chem., Amer. Soc. Of Biochem. Biologists, vol. 275, No. 31, Aug. 4, 2000, pp. 24089-24095.
Jensen et al., "The KCNQ5 potassium channel from mouse . . . ", Mol. Brain Research, Elsevier Science BV, vol. 139, No. 1, Sep. 13, 2005, pp. 52-62.
Lan et al., "Electrophysiological and molecular identification . . . ", Biochimica ET Biophysica Acta. Biomembranes, vol. 1668, Mar. 1, 2005, pp. 223-233.
Database Embl, Dec. 1, 2000, "UI-R-BJ2-bon-h-03-0-UI.s1 . . . ", XP002438197, Embl:BF414224, Database Accession No. BF414224.
Jianfeng et al., "Cloning and mutation analysis of the human potassium . . . ", Neuroreport, vol. 12, No. 17, Dec. 4, 2001, pp. 3733-3739.
Pongs, "Voltage-gated potassium channels: from hyperexcitability . . . ", FEBS Letters, Elsevier, vol. 452, Jun. 4, 1999, pp. 31-35.

* cited by examiner

*Primary Examiner*—Christine J Saoud
*Assistant Examiner*—Jon M Lockard
(74) *Attorney, Agent, or Firm*—Potter Anderson & Corroon LLP

(57) ABSTRACT

Disclosed herein are nucleic acid and polypeptide sequences of a novel rat voltage-gated potassium channel, KCNQ5. Also disclosed herein are methods related to the use of the aforementioned potassium channel.

13 Claims, 2 Drawing Sheets

SEQUENCE LISTING

```
<160> NUMBER OF SEQ ID NOS: 10

<210> SEQ ID NO 1
<211> LENGTH: 2444
<212> TYPE: DNA
<213> ORGANISM: Rattus norvegicus
<220> FEATURE:
<221> NAME/KEY: misc_feature
<222> LOCATION: (80)..(80)
<223> OTHER INFORMATION: n is a, g, t, or c
<220> FEATURE:
<221> NAME/KEY: misc_feature
<222> LOCATION: (109)..(109)
<223> OTHER INFORMATION: n is a, g, t, or c
<220> FEATURE:
<221> NAME/KEY: misc_feature
<222> LOCATION: (2151)..(2151)
<223> OTHER INFORMATION: n is a, g, t, or c

<400> SEQUENCE: 1
gaaagcgagg gacacctcac aaagtgacgc ccccaacagg tccggatttg gaattggaag      60
cggcagaaat ccggacctcn ccgggcctgc tccgcacacc ccgccgccnc cgcccggagc     120
```

```
ccagaccctc ggcttgccgg ccccccaggg cgccccgtcg gctgcgggct tcctcctgca      180
gacctgcccg cgcacatgaa gcggctgccc ccgccgcagg cgccggcgcc ccctcgcgg       240 tgcccgtggt gatgccatgc cccgccacca cgcgggagga gaggagggcg gtgccgccgg      300
gctctgggtg aggagcggcg cggcggcggc ggcggtgggg gggcgccggg gcagcggcat      360
gaaggatgtg gagtccggcc gcggcagggt gctgctgaac tcggcggccg ccaggggcga      420
cggcctgctg ctgctcggca cccgcgcggc ggcgctcggc ggaggcggcg gcggcttgag      480
agagagccgc cggggcaagc aggggggcccg gatgagcctg ctgggaagc cgctctccta     540 caccagcagc cagagctgtc ggcgcaacgt caagtaccgg agggtgcaga actatctgta      600
caacgtgctg gagagacccc gcggctgggc gttcgtctac cacgcgttcg tttttctcct     660
tgtgtttggt tgcttgattt tgtcagtgtt ttctaccatc cctgagcaca caaagttggc     720
ttcaagttgc ctcttaattc tggagttcgt gatgatcgtt gtctttggct tggagttcat     780
cattcgaatc tggtctgcag gttgctgttg tcgttataga ggatggcaag ggagactgag     840
gtttgctcga aagcctttct gtgttataga taccattgtt cttatcgctt caatagcagt     900
tgtttctgca aaaactcagg gtaatatttt cgccacgtca gcgctcagaa gtctccggtt     960
cctacagatc ctgcgtatgg tgcgcatgga cagaagggga gggacctgga agttgctggg    1020
ctccgtggtt tacgctcaca gcaaggaatt aatcacagcc tggtacattg gatttctggt    1080
tcttattttt tcatccttcc ttgtctatct tgtggaaaaa gatgccaata aagagttttc    1140
aacatatgcg gatgctctct ggtggggcac aattacactg acaaccattg gctatggaga    1200
caaaacaccc ctaacttggc tgggaagatt gctctctgca ggcttcgccc ttcttggtat    1260
ttctttcttt gcacttcctg ctggcattct tggctcaggt tttgccttaa agtacagga    1320 acagcaccgc cagaagcatt ttgagaaaag aaggaaccca gctgccaacc tcatccagtg    1380
tgtctggcgt agctatgcag ctgatgagaa gtcggtctcc atcgcaacct ggaagccaca    1440
tctgaaggcc ttgcacacct gcagccctac caagaaagaa caaggggagg cagcaagcag    1500
tcagaagctg agctttaagg agcgagtgcg catggctagc ccaagaggcc agagcattaa    1560
gagcagacaa gcatcggtag gtgaccggag atccccaagc actgacatca ctgctgaggg    1620
cagccccacc aaagtgcaga agagctggag cttcaacgac cgaacccgct tcaggccctc    1680
actacgcctc aagagttccc agccgaagac ggtgatagac gctgacacag cccttggcat    1740
tgacgacgta tacgatgaga aaggatgcca gtgtgacgtg tccgtggagg acctcacccc    1800
accactcaaa accgtcatcc gagccatcag aatcatgaag tttcatgttg caaagcggaa    1860
gtttaaggaa acattacgcc catatgatgt aaaggatgtc attgagcaat actctgctgg    1920
ccatctggac atgctatgta gaattaaaag ccttcaaaca cgcgttgatc aaattcttgg    1980
aaaaggacaa atcacatcag aaactatgtg atcaggacta tacctgagtc ttacatgatg    2040
gcctcatgag ctacaataca tcaagccagg gacatgcata caagttcaga tccagaaaat    2100
ttctacttgt gaaaatgttt cgatgacttc agaattattc attgtcagcc nctgtgtcta    2160
tttggtgcta caaacaaaaa aaaaaagga agaacaaac ccctgatcca agggcttata     2220
aatacacagt gtggagatga accaagggca tttcatattt atagggaagg attggccaac    2280
tgttccattt ctcaccattg catgtacatt gtgtctttcc aattgtttgc gttgttttta    2340
tgaaagagct gcaaaattgt gcaagtggtt caacatgacc aaagtggtat tatgctgctg    2400
ggaagtaaac gtattagata ccaaaaaaaa aaaaaaaaaa aaaa                      2444
```

<210> SEQ ID NO 2
<211> LENGTH: 584
<212> TYPE: PRT
<213> ORGANISM: Rattus norvegicus

<400> SEQUENCE: 2

```
Met Pro Arg His His Ala Gly Gly Glu Glu Gly Gly Ala Ala Gly Leu
1               5                   10                  15

Trp Val Arg Ser Gly Ala Ala Ala Ala Gly Gly Arg Pro Gly
            20                  25                  30

Ser Gly Met Lys Asp Val Glu Ser Gly Arg Gly Arg Val Leu Leu Asn
            35                  40                  45

Ser Ala Ala Arg Gly Asp Gly Leu Leu Leu Gly Thr Arg Ala
50                  55                  60

Ala Ala Leu Gly Gly Gly Gly Gly Leu Arg Glu Ser Arg Arg Gly
65                  70                  75                  80

Lys Gln Gly Ala Arg Met Ser Leu Leu Gly Lys Pro Leu Ser Tyr Thr
                85                  90                  95

Ser Ser Gln Ser Cys Arg Arg Asn Val Lys Tyr Arg Arg Val Gln Asn
            100                 105                 110

Tyr Leu Tyr Asn Val Leu Glu Arg Pro Arg Gly Trp Ala Phe Val Tyr
            115                 120                 125

His Ala Phe Val Phe Leu Leu Val Phe Gly Cys Leu Ile Leu Ser Val
130                 135                 140

Phe Ser Thr Ile Pro Glu His Thr Lys Leu Ala Ser Ser Cys Leu Leu
145                 150                 155                 160

Ile Leu Glu Phe Val Met Ile Val Phe Gly Leu Glu Phe Ile Ile
                165                 170                 175

Arg Ile Trp Ser Ala Gly Cys Cys Cys Arg Tyr Arg Gly Trp Gln Gly
            180                 185                 190

Arg Leu Arg Phe Ala Arg Lys Pro Phe Cys Val Ile Asp Thr Ile Val
            195                 200                 205

Leu Ile Ala Ser Ile Ala Val Val Ser Ala Lys Thr Gln Gly Asn Ile
210                 215                 220

Phe Ala Thr Ser Ala Leu Arg Ser Leu Arg Phe Leu Gln Ile Leu Arg
225                 230                 235                 240

Met Val Arg Met Asp Arg Arg Gly Gly Thr Trp Lys Leu Leu Gly Ser
                245                 250                 255

Val Val Tyr Ala His Ser Lys Glu Leu Ile Thr Ala Trp Tyr Ile Gly
            260                 265                 270

Phe Leu Val Leu Ile Phe Ser Ser Phe Leu Val Tyr Leu Val Glu Lys
            275                 280                 285

Asp Ala Asn Lys Glu Phe Ser Thr Tyr Ala Asp Ala Leu Trp Trp Gly
            290                 295                 300

Thr Ile Thr Leu Thr Thr Ile Gly Tyr Gly Asp Lys Thr Pro Leu Thr
305                 310                 315                 320

Trp Leu Gly Arg Leu Leu Ser Ala Gly Phe Ala Leu Leu Gly Ile Ser
                325                 330                 335

Phe Phe Ala Leu Pro Ala Gly Ile Leu Gly Ser Gly Phe Ala Leu Lys
            340                 345                 350

Val Gln Glu Gln His Arg Gln Lys His Phe Glu Lys Arg Arg Asn Pro
            355                 360                 365

Ala Ala Asn Leu Ile Gln Cys Val Trp Arg Ser Tyr Ala Ala Asp Glu
            370                 375                 380
```

```
Lys Ser Val Ser Ile Ala Thr Trp Lys Pro His Leu Lys Ala Leu His
385                 390                 395                 400

Thr Cys Ser Pro Thr Lys Lys Glu Gln Gly Glu Ala Ala Ser Ser Gln
            405                 410                 415

Lys Leu Ser Phe Lys Glu Arg Val Arg Met Ala Ser Pro Arg Gly Gln
        420                 425                 430

Ser Ile Lys Ser Arg Gln Ala Ser Val Gly Asp Arg Ser Pro Ser
    435                 440                 445

Thr Asp Ile Thr Ala Glu Gly Ser Pro Thr Lys Val Gln Lys Ser Trp
450                 455                 460

Ser Phe Asn Asp Arg Thr Arg Phe Arg Pro Ser Leu Arg Leu Lys Ser
465                 470                 475                 480

Ser Gln Pro Lys Thr Val Ile Asp Ala Asp Thr Ala Leu Gly Ile Asp
            485                 490                 495

Asp Val Tyr Asp Glu Lys Gly Cys Gln Cys Asp Val Ser Val Glu Asp
            500                 505                 510

Leu Thr Pro Pro Leu Lys Thr Val Ile Arg Ala Ile Arg Ile Met Lys
            515                 520                 525

Phe His Val Ala Lys Arg Lys Phe Lys Glu Thr Leu Arg Pro Tyr Asp
530                 535                 540

Val Lys Asp Val Ile Glu Gln Tyr Ser Ala Gly His Leu Asp Met Leu
545                 550                 555                 560

Cys Arg Ile Lys Ser Leu Gln Thr Arg Val Asp Gln Ile Leu Gly Lys
            565                 570                 575

Gly Gln Ile Thr Ser Glu Thr Met
            580

<210> SEQ ID NO 3
<211> LENGTH: 19
<212> TYPE: DNA
<213> ORGANISM: Artificial
<220> FEATURE:
<223> OTHER INFORMATION: First gap, forward primer from rat KCNQ5 EST

<400> SEQUENCE: 3
aagccgctct cctacacca                                              19

<210> SEQ ID NO 4
<211> LENGTH: 19
<212> TYPE: DNA
<213> ORGANISM: Artificial
<220> FEATURE:
<223> OTHER INFORMATION: First gap, reverse primer from rat KCNQ5 EST

<400> SEQUENCE: 4
gagagcaatc ttcccagcc                                              19

<210> SEQ ID NO 5
<211> LENGTH: 20
<212> TYPE: DNA
<213> ORGANISM: Artificial
<220> FEATURE:
<223> OTHER INFORMATION: Second gap, forward primer from rat KCNQ5 EST

<400> SEQUENCE: 5
tggctgggaa gattgctctc                                             20
```

```
<210> SEQ ID NO 6
<211> LENGTH: 19
<212> TYPE: DNA
<213> ORGANISM: Artificial
<220> FEATURE:
<223> OTHER INFORMATION: Second gap, reverse primer from rat KCNQ5 EST

<400> SEQUENCE: 6
ctcagcagtg atgtcagtg                                                 19

<210> SEQ ID NO 7
<211> LENGTH: 20
<212> TYPE: DNA
<213> ORGANISM: Artificial
<220> FEATURE:
<223> OTHER INFORMATION: N-terminus forward primer for rKCNQ5

<400> SEQUENCE: 7
gccatgcccc gccaccacgc                                                20

<210> SEQ ID NO 8
<211> LENGTH: 25
<212> TYPE: DNA
<213> ORGANISM: Artificial
<220> FEATURE:
<223> OTHER INFORMATION: N-terminus reverse primer for rKCNQ5

<400> SEQUENCE: 8
agggcctgaa gcgggttcgg tcgtt                                          25

<210> SEQ ID NO 9
<211> LENGTH: 19
<212> TYPE: DNA
<213> ORGANISM: Artificial
<220> FEATURE:
<223> OTHER INFORMATION: C-terminus forward primer for rKCNQ5

<400> SEQUENCE: 9
ggctgggaag attgtctct                                                 19

<210> SEQ ID NO 10
<211> LENGTH: 23
<212> TYPE: DNA
<213> ORGANISM: Artificial
<220> FEATURE:
<223> OTHER INFORMATION: C-terminus reverse primer for rKCNQ5

<400> SEQUENCE: 10
cgcttagaaa ggaaacaaag aac                                            23
```

RAT KCNQ5 VOLTAGE-GATED POTASSIUM CHANNEL

CROSS-REFERENCE TO RELATED APPLICATION

This application claims the benefit of U.S. Provisional Application Ser. No. 60/760,249 filed Jan. 19, 2006, which is incorporated by reference herein in its entirety.

FIELD OF THE INVENTION

Disclosed herein is a novel rat voltage gated potassium channel KCNQ5 gene, nucleic acid, protein, vectors, and methods of use thereof.

BACKGROUND OF THE INVENTION

Ion channels are cellular proteins that regulate the flow of ions, including calcium, potassium, sodium and chloride, into and out of cells. These channels affect such processes as nerve transmission, muscle contraction and cellular secretion. Among the ion channels, potassium channels are the most ubiquitous and diverse, being found in a variety of animal cells such as nerve, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are membrane-spanning proteins that generally act to hyperpolarize neurons and muscle cells. Physiological studies indicate that potassium currents are found in most cells and are associated with a wide range of functions, including the regulation of the electrical properties of excitable cells. Depending on the type of potassium channel, its functional activity can be controlled by transmembrane voltage, different ligands, protein phosphorylation, or other second messengers (see, e.g., U.S. Pat. No. 6,893,858).

The potassium channel family possesses approximately seventy members in mammalian tissues. The recently identified KCNQ subfamily (Kv7) has been shown to play an important functional role as determinants of cell excitability. Recent evidence indicates that the KCNQ potassium channel sub-units form the molecular basis for M-current activity in several tissue types. This gene family has evolved to contain at least five major sub-units designated KCNQ1 through KCNQ5 (Kv7.1-7.5). These sub-units have been shown to co-assemble to form both heteromeric and homomeric functional ion channels.

Voltage dependant potassium channels are key regulators of the resting membrane potential and modulate the excitability of electrically active cells, such as neurons or myocytes. Several classes of voltage dependant potassium ($K^+$) channels have been cloned (see, e.g., Lerche C et al., J. Biol. Chem. 275:22395-22400 (2000)).

Mutations in four of the five KCNQ potassium channel genes are implicated in diverse diseases, causing cardiac LQT syndrome (KCNQ1), epilepsy (KCNQ2, and 3), congenital deafness (KCNQ4). In rat genome, however, only four KCNQ channels have been identified.

Potassium channels are involved in a number of physiological processes, including regulation of heartbeat, dilation of arteries, release of insulin, excitability of nerve cells, and regulation of renal electrolyte transport.

Herein, Applicants describe a novel gene, and uses for, the rat KCNQ5 (rKCNQ5) that has been identified from the expressed sequence tags (ESTs) using RT-PCR (reverse transcription-polymerase chain reaction) and RACE (rapid amplification of cDNA ends).

SUMMARY OF THE INVENTION

One aspect is directed to a novel rat voltage gated potassium channel KCNQ5 gene, nucleic acid, protein, and vectors, as well as uses for same. KCNQ5 is useful for identification and development of activators and inhibitors to treat a variety of central and peripheral nerve disorders. Also disclosed herein is the cloning of the novel rat gene KCNQ5.

One embodiment provides an isolated polynucleotide encoding all or a portion of an rKCNQ5 polypeptide.

Another embodiment provides an isolated polynucleotide comprising SEQ ID NO:1. A further aspect relates to a polynucleotide encoding SEQ ID NO:2. Another embodiment provides for a nucleic acid sequence encoding a polypeptide having at least 90% identity with SEQ ID NO:1. A further embodiment relates to a nucleic acid molecule which is capable of hybridizing under highly stringent conditions to SEQ ID NO:1. Yet another embodiment provides for a variant of SEQ ID NO:1. A further embodiment provides for a nucleic acid molecule that is complementary to the aforementioned sequences.

Another aspect provides for an isolated polynucleotide described above wherein the isolated polynucleotide is DNA.

Another embodiment provides for an isolated polynucleotide described above wherein the isolated polynucleotide is RNA.

Another aspect provides for a vector comprising an isolated polynucleotide described above.

In a preferred embodiment, the expression vector comprises the polynucleotide sequence of SEQ ID NO:1.

A further embodiment is for a host cell transformed with the vector described above.

The host cell can be a prokaryotic cell or a eukaryotic cell.

Another embodiment provides for an isolated polypeptide comprising an amino acid sequence, or a fragment thereof, for a rat KCNQ5 protein. A further embodiment provides for an isolated polypeptide comprising the amino acid sequence of SEQ ID NO:2. Another embodiment provides a variant of the aforementioned sequence. Yet another embodiment provides an isolated polypeptide comprising one or more non human polypeptides which are more than 90% identical to the amino acid sequence of SEQ ID NO:2.

A further aspect is for a KCNQ dimeric channel comprising at least one KCNQ5 subunit which is the aforementioned isolated polypeptide. Another aspect is for a KCNQ tetrameric channel comprising at least one KCNQ5 subunit which is the aforementioned isolated polypeptide.

Another aspect for is a method of screening for agents, the method comprising:

(a) contacting an agent with an rKCNQ5 molecule; and (b) detecting an effect of said agent on rKCNQ5 activity;

wherein detection of a decrease or an increase in rKCNQ5 activity is indicative of an agent being a modulator of rKCNQ5.

An additional aspect is for a method of screening for agents, the method comprising:

(a) contacting a cell with an agent; and
(b) determining the level of expression of an rKCNQ5 molecule;

wherein detection of a decrease or an increase in rKCNQ5 expression is indicative of an agent being a modulator of rKCNQ5.

Another aspect is for methods of inducing or maintaining bladder control, treatment or prevention of urinary incontinence, or treatment or prevention of neuropathic pain in a mammal, the method comprising administering to a mammal in need thereof of a pharmacologically effective amount of the agent identified by any of the aforementioned methods.

Another embodiment provides for a method for identifying polypeptides capable of binding to rKCNQ5 comprising:
(a) applying a mammalian two-hybrid procedure in which a sequence encoding a rKCNQ5 polypeptide is carried by one hybrid vector and sequence from a cDNA or genomic DNA library is carried by the second hybrid vector;
(b) transforming the host cell with the vectors;
(c) isolating positive transformed cells; and
(d) extracting said second hybrid vector to obtain a sequence encoding a polypeptide which binds to the rKCNQ5 polypeptide.

Another aspect is for a method of screening a subject for KCNQ5 mutation comprising:
(a) measuring KCNQ5 activity;
(b) measuring rKCNQ5 activity; and
(c) comparing the measured activity in steps (a) and (b), wherein an increase or decrease is indicative of a mutation.

A further aspect is for a method for detecting KCNQ5 polypeptide comprising detecting binding of antibody selected from the group consisting of
(a) an antibody which selectively binds a KCNQ5 polypeptide comprising SEQ ID NO:2; and
(b) an antibody which selectively binds a KCNQ5 polypeptide fragment comprising at least 8 contiguous amino acids from SEQ ID NO:2;

to a molecule in a sample suspected of containing a KCNQ5 polypeptide, wherein the antibody is contacted with the sample under conditions that permit specific binding with any KCNQ5 polypeptide present in the sample and binding of the antibody to the molecule in the sample indicates the presence of KCNQ5.

Another embodiment provides for a method for determining whether a KCNQ5 gene has been mutated or deleted comprising detecting, in a sample of cells or tissue from a subject, the presence or absence of a genetic alteration characterized by at least one of an alteration affecting the integrity of a gene encoding a KCNQ5 protein or the misexpression of a KCNQ5 gene, wherein the detecting step is performed with at least one of a probe or primer comprising at least 12 contiguous nucleotides from nucleotides 257-2008 of SEQ ID NO:1.

An additional aspect is for a method of identifying KCNQ5 variants comprising screening a combinatorial library comprising rKCNQ5 mutants for KCNQ5 agonists or antagonists.

A further embodiment provides for a method of isolating a KCNQ5 polypeptide comprising:
(a) contacting an rKCNQ5 antibody with a sample suspected of containing a KCNQ5 polypeptide; and
(b) isolating an rKCNQ5 antibody-KCNQ5 polypeptide complex from the sample.

Another embodiment provides for a method of producing a KCNQ5 polypeptide comprising:
(a) culturing a transformed host cell comprising an expression vector comprising an isolated polynucleotide selected from the group consisting of:
(i) a polynucleotide encoding a polypeptide having at least 90% identity with the amino acid sequence set forth in SEQ ID NO:2;
(ii) a polynucleotide which hybridizes to (i) under highly stringent conditions; and
(iii) a polynucleotide complementary to (i) or (ii);
in a suitable medium such that a KCNQ5 polypeptide is produced; and
(b) optionally, recovering the KCNQ5 polypeptide of step (a).

Another aspect is for a method for the treatment of a mammal in need of increased KCNQ5 activity comprising administering to the mammal in need thereof a therapeutically effective amount of an rKCNQ5 polynucleotide or polypeptide.

A further aspect is for a method of the treatment of a mammal in need of decreased KCNQ5 activity comprising administering to the mammal in need thereof a therapeutically effective amount of an rKCNQ5 antisense polynucleotide or an rKCNQ5 antibody.

An additional embodiment provides for a method for obtaining anti-rKCNQ5 antibodies comprising:
(a) immunizing an animal with an immunogenic rKCNQ5 polypeptide or an immunogenic portion thereof unique to an rKCNQ5 polypeptide; and
(b) isolating from the animal antibodies that specifically bind to an rKCNQ5 polypeptide.

A further aspect is for a method of developing a sensor cell for determining the activity of a gene comprising:
(a) providing a homogenous population of cells, wherein each of the cells comprises a signal transduction system;
(b) introducing into the population of cells an isolated genomic construct comprising an rKCNQ5 promoter operably linked to a targeting sequence, wherein:
(i) the targeting sequence comprises a region of homology to a target gene sufficient to promote homologous recombination of the isolated genomic construct following introduction into the cells;
(ii) the rKCNQ5 promoter is heterologous to the target gene;
(iii) following recombination the promoter controls transcription of an mRNA that encodes a polypeptide comprising an activatable domain; and
(iv) the polypeptide is capable, upon activation of the activatable domain, of altering the signal detected from the signal transduction system;
(c) incubating the population of cells under conditions which cause expression of the protein;
(d) incubating the population of cells under conditions which cause activation of the activatable domain of the polypeptide; and
(e) selecting cells that have altered the signal detected from the signal transduction system.

Another aspect is for a method for the production of a KCNQ5 polypeptide comprising:
(a) providing a homogenous population of cells;
(b) introducing into the population of cells an isolated genomic construct comprising a promoter operably linked to an rKCNQ5 targeting sequence, wherein
(i) the rKCNQ5 targeting sequence comprises a region of homology to a KCNQ5 target gene sufficient to promote homologous recombination of the isolated genomic construct following introduction into the cells;

(ii) the promoter is heterologous to the KCNQ5 target gene; and (iii) following recombination the promoter controls transcription of an mRNA that encodes a KCNQ5 polypeptide; and (c) incubating the population of cells under conditions which cause expression of the KCNQ5 polypeptide.

Another embodiment provides for a method for assaying the ability of a mutant rKCNQ5 polypeptide to encode a functional ion channel comprising:

(a) transfecting a host cell with a polynucleotide encoding the mutant rKCNQ5 polypeptide;

(b) expressing the mutant KCNQ5 polypeptide in the host cell; and (c) electrophysiologically measuring the ion current magnitude of the mutant rKCNQ5 polypeptide.

Another embodiment is for a method for preventing in a subject a disease or condition that would benefit from modulation of KCNQ5 activity and/or expression comprising administering to the subject an rKCNQ5 polypeptide or agent which modulates at least one KCNQ5 polypeptide expression or at least one KCNQ5 activity.

A further embodiment provides for a kit for detecting KCNQ5 polypeptide or polynucleotide comprising:

(a) a labeled compound or agent capable of detecting an rKCNQ5 polypeptide or polynucleotide in a biological sample;

(b) means for determining the amount of rKCNQ5 polypeptide or polynucleotide in the sample;

(c) means for comparing the amount of rKCNQ5 polypeptide or polynucleotide in the sample with a standard; and (d) optionally, instructions for using the kit to detect rKCNQ5 polypeptide or polynucleotide.

Another embodiment is for a kit for identifying modulators of rKCNQ5 activity comprising:

(a) a cell or composition comprising an rKCNQ5 polypeptide;

(b) means for determining rKCNQ5 polypeptide activity; and (c) optionally, instructions for using the kit to identify modulators of KCNQ5 activity.

A further embodiment is for a kit for diagnosing a disorder associated with aberrant KCNQ5 expression and/or activity in a subject comprising:

(a) a reagent for determining expression of rKCNQ5 polypeptide or polynucleotide;

(b) a control to which the results of the subject are compared; and (c) optionally, instructions for using the kit for diagnostic purposes.

Other objects and advantages will become apparent to those skilled in the art upon reference to the detailed description that hereinafter follows.

DESCRIPTION OF FIGURES

As shown in FIG. 1B, KCNQ5 current is sensitive to both standard KCNQ enhancing agent retigabine and a KCNQ selective blocker XE991. In other words, retigabine increased the channel current amplitude whereas XE 991 decreased the current amplitude.

DETAILED DESCRIPTION OF THE INVENTION

Figure 1:
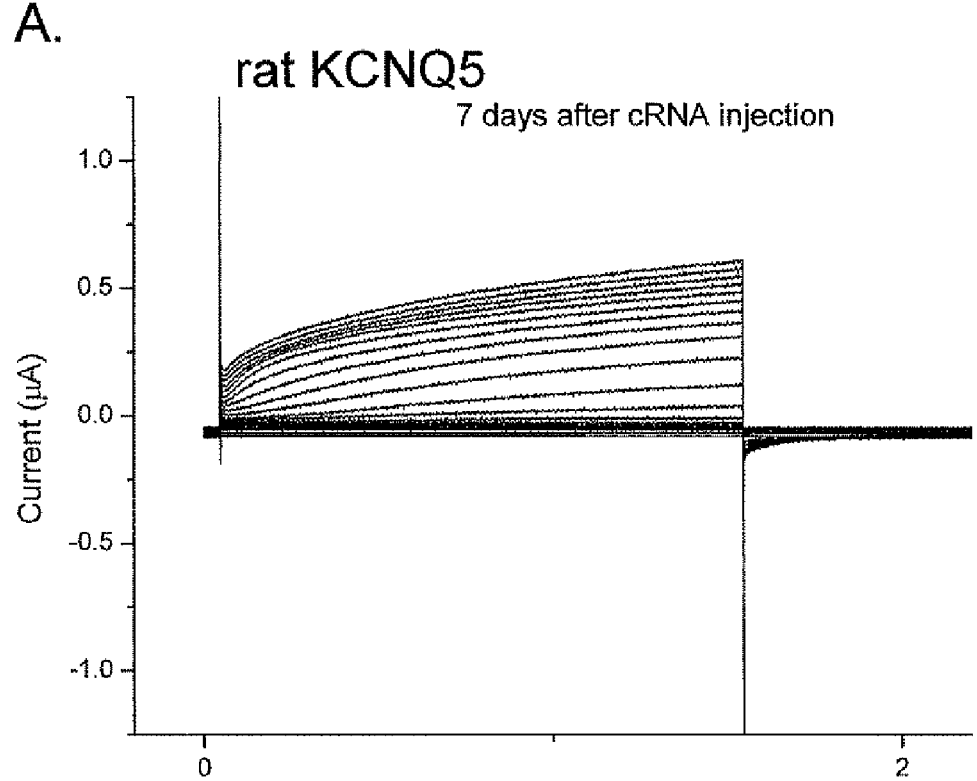
FIG. 1 shows the functional expression of rat KCNQ5 in Xenopus laevis oocytes as set forth in Example 4. cRNAs of rKCNQ5 were injected directly into Xenopus laevis oocytes and the electrophysiological recordings were performed 48-72 hours after RNA injection using two-electrode voltage clamp recording (FIG. 1A). The electrodes were filled with 3 M KCl solution with resistances ranging from 0.5 to 1.5 MΩ.
Figure 1:
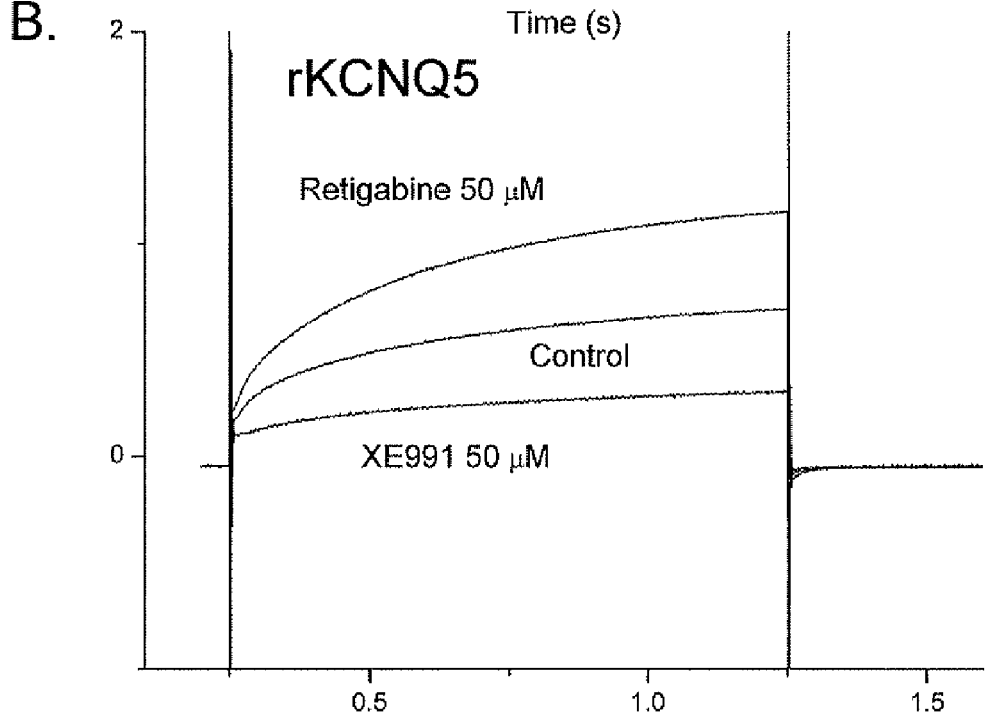

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

One aspect is related to a novel rat voltage gated potassium channel protein KCNQ5, and the gene which encodes it, which is useful for identification and development of activators and inhibitors to treat a variety of central and peripheral nerve disorders.

Another aspect describes a novel KCNQ5 (rKCNQ5) gene, which was identified from the expressed sequence tags (ESTs) using RT-PCR (reverse transcription-polymerase chain reaction) and RACE (rapid amplification of cDNA ends).

I. Definitions

In the context of this disclosure, a number of terms shall be utilized.

As used herein, the term "about" or "approximately" means within 20%, preferably within 10%, and more preferably within 5% of a given value or range.

"Altered levels" refers to the production of gene product(s) in organisms in amounts or proportions that differ from that of normal or non-transformed organisms. Overexpression of the polypeptide may be accomplished by first construction a chimeric gene or chimeric construct in which the coding region is operably linked to a promoter capable of directing expression of a gene or construct in the desired tissues at the desired stage of development. For reasons of convenience, the chimeric gene or chimeric construct may comprise promoter sequences and translation leader sequences derived from the same genes. 3' noncoding sequences encoding transcription termination signals may also be provided. The instant chimeric gene or chimeric construct can then be constructed. The choice of plasmid vector is dependant upon the method that will be used to transform host cells. The skilled artisan is well aware of the genetic elements that must be present on the plasmid vector in order to successfully transform, select and propagate host cells containing the chimeric gene or chimeric construct. The skilled artisan will also recognize that different independent transformation events will result in different levels and patterns of expression (see, e.g., De Almedia E R P et al., Mol. Genet. Genomics 218:78-86 (1989)), and thus that multiple events must be screened in order to obtain lines displaying the desired expression level and pattern. Such screening may be accomplished by southern analysis of DNA, northern analysis of mRNA expression, western or immunocytochemical analysis of protein expression, or phenotypic analysis.

An "antibody" includes an immunoglobulin molecule capable of binding an epitope present on an antigen. As used herein, the term encompasses not only intact immunoglobulin molecules such as monoclonal and polyclonal antibodies, but also anti-idotypic antibodies, mutants, fragments, fusion proteins, bi-specific antibodies, humanized proteins, and modifications of the immunoglobulin molecule that comprises an antigen recognition site of the required specificity.

The term "cDNAs" includes complementary DNA, that is mRNA molecules present in a cell or organism made into cDNA with an enzyme such as reverse transcriptase. A "cDNA library" includes a collection of mRNA molecules present in a cell or organism, converted into cDNA molecules with the enzyme reverse transcriptase, then inserted into vectors. The library can then be probed for the specific cDNA (and thus mRNA) of interest.

As used herein, an rKCNQ5 "chimeric protein" or "fusion protein" comprises an rKCNQ5 polypeptide operably linked to a non-rKCNQ5 polypeptide. An "rKCNQ5 polypeptide" refers to a polypeptide having an amino acid sequence corresponding to rKCNQ5 polypeptide, whereas a "non-rKCNQ5 polypeptide" refers to a polypeptide having an amino acid sequence corresponding to a protein which is not substantially homologous to the rKCNQ5 protein, for example, a protein which is different from the rKCNQ5 protein and which is derived from the same or a different organism. Within an rKCNQ5 fusion protein, the rKCNQ5 polypeptide can correspond to all or a portion of an rKCNQ5 protein. In a preferred embodiment, an rKCNQ5 fusion protein comprises at least one biologically active portion of an rKCNQ5 protein. Within the fusion protein, the term "operably linked" is intended to indicate that the rKCNQ5 polypeptide and the non-rKCNQ5 polypeptide are fused in-frame to each other. The non-rKCNQ5 polypeptide can be fused to the N-terminus or C-terminus of the rKCNQ5 polypeptide.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein, or enzyme.

The term "complementary" is used to describe the relationship between nucleotide bases that are capable to hybridizing to one another. For example, with respect to DNA, adenosine is complementary to thymine and cytosine is complementary to guanine.

The terms "effective amount", "therapeutically effective amount", and "effective dosage" as used herein, refer to the amount of an effector molecule that, when administered to a mammal in need, is effective to at least partially ameliorate conditions related to or adverse conditions of, for example, the central nervous system (CNS) and peripheral systems, including various types of pain such as, for example, somatic, cutaneous, or visceral pain caused by, for example burn, bruise, abrasion, laceration, broken bone, torn ligament, torn tendon, torn muscle, viral, bacterial, protozoal or fungal infection, contact dermatitis, inflammation (caused by, e.g., trauma, infection, surgery, burns, or diseases with an inflammatory component), cancer, toothache; neuropathic pain caused by, for example, injury to the central or peripheral nervous system due to cancer, HIV (human immunodeficiency virus) infection, tissue trauma, infection, autoimmune disease, diabetes, arthritis, diabetic neuropathy, trigeminal neuralgia, or drug administration; treating anxiety caused by, for example, panic disorder, generalized anxiety disorder, or stress disorder, particularly acute stress disorder, affective disorders, Alzheimer's disease, ataxia, CNS damage caused by trauma, stroke or neurodegenerative illness, cognitive deficits, compulsive behavior, dementia, depression, Huntington's disease, mania, memory impairment, memory disorders, memory dysfunction, motion disorders, motor disorders, age-related memory loss, neurodegenerative diseases, Parkinson's disease and Parkinson-like motor disorders, phobias, Pick's disease, psychosis, schizophrenia, spinal cord damage, tremor, seizures, convulsions, epilepsy, Stargardt-like macular dystrophy, cone-rod macular dystrophy, Salla disease, epilepsy, muscle relaxants, fever reducers, anxiolytics, antimigraine agents, analgesics, bipolar disorders, unipolar depression, functional bowel disorders (e.g., dyspepsia and irritable bowl syndrome), diarrhea, constipation, various types of urinary incontinence (e.g., urge urinary incontinence, stress urinary incontinence, overflow urinary incontinence or unconscious urinary incontinence, and mixed urinary incontinence), urinary urgency, bladder instability, neurogenic bladder, hearing loss, tinnitus, glaucoma, cognitive disorders, chronic inflammatory and neuralgic pain; for preventing and reducing drug dependence or tolerance for treatment of, for example, cancer, inflammation, ophthalmic diseases, and various CNS disorders.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular, or secreted. The term "intracellular" means something that is inside a cell. The term "extracellular" means something that is outside a cell. A substance is "secreted" by a cell if it appears in significant measure outside the cell, from somewhere on or inside the cell. "Antisense inhibition" refers to the production of antisense RNA transcripts capable of suppression the expression of the target protein. "Overexpression" refers to the production of a gene product in an organism that exceeds levels of production in normal or non-transformed organisms. "Suppression" refers to suppressing the expression of foreign or endogenous genes or RNA transcripts.

The term "expression system" means a host cell and compatible vector under suitable conditions, e.g. for the expression of a protein coded for by foreign DNA carried by the vector and introduced to the host cell.

The term "gene" means a DNA sequence, including regulatory sequences preceding (5' non-coding sequences) and following (3' non-coding sequences) the coding sequence, that codes for or corresponds to a particular sequence of amino acids which comprise all or part of one or more proteins or enzymes. "Native gene" refers to a gene as found in nature with its own regulatory sequences. "Chimeric gene" or "chimeric construct" refers to any gene or construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The term "genetically modified" includes a cell containing and/or expressing a foreign gene or nucleic acid sequence which in turn modifies the genotype or phenotype of the cell or its progeny. This term includes any addition, deletion, or disruption to a cell's endogenous nucleotides.

A "gene product" includes an amino acid (e.g., peptide or polypeptide) generated when a gene is transcribed and translated.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operably associated with a different gene than the one it is operably associated with in nature.

The term "homomeric" as used herein refers to an ion channel comprising only one type of subunit. For example, a homomeric dimer ("homodimer") KCNQ channel could be composed of two identical KCNQ5 polypeptide subunits. A homomeric tetramer ("homotetramer") could be composed of four identical KCNQ5 polypeptide subunits. The term "heteromeric" as used herein refers to an ion channel comprising at least two different subunits. For example, a heteromeric dimer ("heterodimer") KCNQ channel could be composed of one KCNQ5 polypeptide subunit and one KCNQ3 subunit, or a heterodimer KCNQ channel could be composed of one KCNQ5 polypeptide subunit and a different KCNQ5 polypeptide subunit. A heteromeric tetramer ("heterotetramer") KCNQ channel could be composed of 1, 2, 3, or 4 KCNQ5 polypeptide subunits, provided that if all four subunits are KCNQ5 polypeptide subunits that at least one of the subunits is different from the other three.

"Homologous" refers to the degree of sequence similarity between two polymers (i.e. polypeptide molecules or nucleic acid molecules). The homology percentage figures referred to herein reflect the maximal homology possible between the two polymers, i.e., the percent homology when the two polymers are so aligned as to have the greatest number of matched (homologous) positions. The terms "homologous" and "homology" also refer to the relationship between proteins that possess a "common evolutionary origin", including proteins from superfamilies (e.g., the immunoglobulin superfamily) and homologous proteins from different species (e.g., myosin light chain, etc.) (see, e.g., Reeck G R et al., Cell 50:667 (1987)). Such proteins (and their encoding genes) have sequence homology, as reflected by their sequence similarity, whether in terms of percent similarity or the presence of specific residues or motifs at conserved positions. Accordingly, the term "sequence similarity" refers to the degree of identity or correspondence between nucleic acid or amino acid sequences of proteins that may or may not share a common evolutionary origin (see Reeck G R et al., supra). However, in common usage and in the instant application, the term "homologous", when modified with an adverb such as "highly", may refer to sequence similarity and may or may not relate to a common evolutionary origin.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions×100). The percent identity between the two sequences is a function of the number of identical positions shared by the sequences, taking into account the number of gaps, and the length of each gap, which are introduced for optimal alignment of the two sequences.

The comparison of sequences and determination of percent identity between two sequences can be accomplished using a mathematical algorithm. A non-limiting example of a mathematical algorithm utilized for comparison of sequences is the algorithm of Karlin S and Altschul S F, Proc. Natl. Acad. Sci. USA 87:2264-68 (1990), modified as in Karlin S and Altschul S F, Proc. Natl. Acad. Sci. USA 90:5873-77 (1993). Such an algorithm is incorporated into the NBLAST and XBLAST programs (version 2.0) of Altschul S F et al., J. Mol. Biol. 215:403-10 (1990). BLAST nucleotide searches can be performed with the NBLAST program score=100, wordlength=12 to obtain nucleotide sequences homologous to the nucleic acid molecules. BLAST protein searches can be performed with the XBLAST program, score=50, wordlength=3 to obtain amino acid sequences homologous to the protein molecules. To obtain gapped alignments for comparison purposes, Gapped BLAST can be utilized as described in Altschul S F et al., Nucleic Acids Res. 25:3389-3402 (1997). When utilizing BLAST and Gapped BLAST programs, the default parameters of the respective programs (e.g., XBLAST and NBLAST) can be used. Another preferred, non-limiting algorithm utilized for the comparison of sequences is the algorithm of Myers E W and Miller W, Comput. Appl. Biosci. 4:11-17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Another non-limiting example of a mathematical algorithm utilized for the alignment of protein sequences is the Lipman-Pearson algorithm (Lipman D J and Pearson W R, Science 227:1435-41 (1985)). When using the Lipman-Pearson algorithm, a PAM250 weight residue table, a gap length penalty of 12, a gap penalty of 4, and a Kutple of 2 can be used. A preferred, non-limiting example of a mathematical algorithm utilized for the alignment of nucleic acid sequences is the Wilbur-Lipman algorithm (Wilbur W J and Lipman D J, Proc. Natl. Acad. Sci. USA 80:726-30 (1983)). When using the Wilbur-Lipman algorithm, a window of 20, gap penalty of 3, Ktuple of 3 can be used. Both the Lipman-Pearson algorithm and the Wilbur-Lipman algorithm are incorporated, for example, into the MEGALIGN program (e.g., version 3.1.7) which is part of the DNASTAR sequence analysis software package.

Additional algorithms for sequence analysis are known in the art, and include ADVANCE and ADAM, described in Torelli A and Robotti C A, Comput. Appl. Biosci. 10:3-5 (1994); and FASTA, described in Pearson W R and Lipman D J, Proc. Natl. Acad. Sci. USA 85:2444-48 (1988).

In a preferred embodiment, the percent identity between two amino acid sequences is determined using the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

Protein alignments can also be made using the Geneworks global protein alignment program (e.g., version 2.5.1) with the cost to open gap set at 5, the cost to lengthen gap set at 5, the minimum diagonal length set at 4, the maximum diagonal offset set at 130, the consensus cutoff set at 50% and utilizing the Pam 250 matrix.

The nucleic acid and protein sequences can further be used as a "query sequence" to perform a search against public databases to, for example, identify other family members or related sequences. Such searches can be performed using the NBLAST and XBLAST programs (version 2.0) of Altschul S F et al., J. Mol. Biol. 215:403-10 (1990). BLAST nucleotide searches can be performed with the NBLAST program, score=100, wordlength=12 to obtain nucleotide sequences homologous to rKCNQ5 nucleic acid molecules. BLAST protein searches can be performed with the XBLAST program, score=50, wordlength=3 to obtain amino acid sequences homologous to rKCNQ5 protein molecules. To obtain gapped alignments for comparison purposes, Gapped BLAST can be utilized as described in Altschul S F et al., Nucleic Acids Res. 25:3389-3402 (1997). When utilizing BLAST and Gapped BLAST programs, the default parameters of the respective programs (e.g., XBLAST and NBLAST) can be used. For example, the nucleotide sequences can be analyzed using the default Blastn matrix 1-3 with gap penalties set at: existence 11 and extension 1. The amino acid sequences can be analyzed using the default settings: the Blosum62 matrix with gap penalties set at existence 11 and extension 1.

The term "host cell" means any cell of any organism that is selected, modified, transformed, grown, or used or manipulated in any way, for the production of a substance by the cell, for example the expression by the cell of a gene, a DNA or RNA sequence, a protein, or an enzyme.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (Sambrook, J. et al. (eds.), *Molecular Cloning: A Laboratory Manual* (2d Ed. 1989) Cold Spring Harbor Laboratory Press, NY. Vols. 1-3 (ISBN 0-87969-309-6)). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (Sambrook et al. (eds.), *Molecular Cloning: A Laboratory Manual* (2d Ed. 1989) Cold Spring Harbor Laboratory Press, NY. Vols. 1-3. (ISBN 0-87969-309-6), 9.50-9.51).

"Inhibitors", "activators", "openers", or "modulators" of voltage-gated potassium channels comprising a KCNQ subunit refer to inhibitory or activating molecules identified using in vitro and in vivo assays for KCNQ channel function. In particular, inhibitors, activators, and modulators refer to compounds that increase KCNQ channel function, thereby reducing pain in a subject. "Inhibitors" are compounds that decrease, block, prevent, delay activation, inactivate, desensitize, or down regulate the channel, or speed or enhance deactivation. "Activators" are compounds that increase, open, activate, facilitate, enhance activation, sensitize or up regulate channel activity, or delay or slow inactivation. Such assays for inhibitors and activators also include, e.g., expressing recombinant KCNQ in cells or cell membranes and then measuring flux of ions through the channel directly or indirectly.

The term "isolated" means that the material is removed from its original or native environment (e.g., the natural environment if it is naturally occurring). Therefore, a naturally-occurring polynucleotide or polypeptide present in a living animal is not isolated, but the same polynucleotide or polypeptide, separated or modified by human intervention from some or all of the coexisting materials in the natural system, is isolated. For example, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Such polynucleotides could be part of a vector and/or such polynucleotides or polypeptides could be part of a composition, and still be isolated in that such vector or composition is not part of the environment in which it is found in nature. Similarly, the term "substantially purified" refers to a substance, which has been separated or otherwise removed, through human intervention, from the immediate chemical environment in which it occurs in nature. Substantially purified polypeptides or nucleic acids may be obtained or produced by any of a number of techniques and procedures generally known in the field (see, e.g., Scopes R (1987) In: Protein purification: principles and practice, Springer-Verlag, NY. General protein and DNA/RNA purification references: Current protocols in molecular biology, Green publishing associates and John Wiley & Sons).

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

The term "modulate" refers to the suppression, enhancement or induction of a function. For example, "modulation" or "regulation" of gene expression refers to a change in the activity of a gene. Modulation of expression can include, but is not limited to, gene activation and gene repression. "Modulate" or "regulate" also refers to methods, conditions, or agents which increase or decrease the biological activity of a protein, enzyme, inhibitor, signal transducer, receptor, transcription activator, cofactor and the like. This change in activity can be an increase or decrease of mRNA translation, DNA transcription, and/or mRNA or protein degradation, which may in turn correspond to an increase or decrease in biological activity. Such enhancement or inhibition may be contingent upon occurrence of a specific event, such as activation of a signal transduction pathway and/or may be manifest only in particular cell types.

"Modulated activity" refers to any activity, condition, disease or phenotype that is modulated by a biologically active form of a protein. Modulation may be affected by affecting the concentration of biologically active protein, e.g., by regulating expression or degradation, or by direct agonistic or antagonistic effect as, for example, through inhibition, activation, binding, or release of substrate, modification either chemically or structurally, or by direct or indirect interaction which may involve additional factors.

As used herein, a "naturally-occurring" nucleic acid molecule refers to an RNA or DNA molecule having a nucleotide sequence that occurs in nature (e.g., encodes a natural protein).

As used herein, "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single-stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

The term "operably linked" means that a nucleic acid molecule, i.e., DNA, and one or more regulatory sequences (e.g., a promoter or portion thereof) are connected in such a way as to permit transcription of mRNA from the nucleic acid molecule or permit expression of the product (i.e., a polypeptide) of the nucleic acid molecule when the appropriate molecules are bound to the regulatory sequences. Within a fusion construct, the term "operably linked" is intended to indicate that the rKCNQ5 polynucleotide and a non-rKCNQ5 polynucleotide are fused in-frame to each other. The non-rKCNQ5 polynucleotide can be fused 3' or 5' to the rKCNQ5 polynucleotide.

The term "percent homology" refers to the extent of amino acid sequence identity between polynucleotides or polypeptides. The homology between any two polynucleotides or polypeptides is a direct function of the total number of matching nucleotides or amino acids at a given position in either sequence, e.g., if half of the total number of nucleotides in either of the sequences are the same then the two sequences are said to exhibit 50% homology.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases such as, for example, thio-uracil, thio-guanine, and fluoro-uracil.

It is contemplated that where the nucleic acid molecule is RNA, the T (thymine) in non-RNA sequences provided herein is substituted with U (uracil). For example, SEQ ID NO:1 is disclosed herein as a cDNA sequence. Thus, It would be obvious to one of ordinary skill in the art that an RNA molecule comprising sequences from this sequences, for example, would have T substituted with U.

The term "polypeptide" includes a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of an "upstream" and a "downstream" primer, and a catalyst of polymerization, such as a DNA polymerase, and typically a thermally-stable polymerase enzyme. Methods for PCR are well known in the art, and are taught, for example, in MacPherson et al., IRL Press at Oxford University Press (1991). All processes of producing replicate copies of a polynucleotide, such as PCR or gene cloning, are collectively referred to herein as "replication". A primer can also be used as a probe in hybridization reactions, such as Southern or Northern blot analyses (see, e.g., Sambrook, J., Fritsh, E. F., and Maniatis, T. Molecular Cloning: A Laboratory Manual, 2nd ed., Cold Spring Harbor Laboratory, Cold Spring Harbor Laboratory Press, Cold Spring Harbor, N.Y., 1989).

A "probe" when used in the context of polynucleotide manipulation includes an oligonucleotide that is provided as a reagent to detect a target present in a sample of interest by hybridizing with the target. Usually, a probe will comprise a label or a means by which a label can be attached, either before or subsequent to the hybridization reaction. Suitable labels include, but are not limited to, radioisotopes, fluorochromes, chemiluminescent compounds, dyes, and proteins, including enzymes.

A "promoter sequence" is a DNA regulatory region capable of binding RNA polymerase in a cell and initiating transcription of a downstream (3' direction) coding sequence. For purposes herein, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined, for example, by mapping with nuclease S1), as well as protein binding domains (consensus sequences) responsible for the binding of RNA polymerase.

The term "purified" as used herein refers to material that has been isolated under conditions that reduce or eliminate the presence of unrelated materials, that is, contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure; and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including, for example, centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. A purified material may contain less than about 50%, preferably less than about 75%, and most preferably less than about 90%, of the cellular components with which it was originally associated. The "substantially pure" indicates the highest degree of purity which can be achieved using standard purification techniques known in the art.

The term "test compound" includes compounds with known chemical structure but not necessarily with a known function or biological activity. Test compounds could also have unidentified structures or be mixtures of unknown compounds, for example from crude biological samples such as plant extracts. Large numbers of compounds could be randomly screened from "chemical libraries" which refers to collections of purified chemical compounds or collections of crude extracts from various sources. The chemical libraries may contain compounds that were chemically synthesized or purified from natural products. The compounds may comprise inorganic or organic small molecules or larger organic compounds such as, for example, proteins, peptides, glycoproteins, steroids, lipids, phospholipids, nucleic acids, and lipoproteins. The amount of compound tested can very depending on the chemical library, but, for purified (homogeneous) compound libraries, 10 µM is typically the highest initial dose tested. Methods of introducing test compounds to cells are well known in the art.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell, or cells of a different genus or species. Accordingly, a further embodiment is for a host cell transformed with the vector described above. In one embodiment, the host cell is a prokaryotic cell. In a further embodiment, the host cell is a eukaryotic cell. In a preferred embodiment, the host cell is an *E. coli* cell.

The term "variant" may also be used to indicate a modified or altered gene, DNA sequence, enzyme, cell, etc. Encompassed within the term "variant(s)" are nucleotide and amino acid substitutions, additions or deletions. Also, encompassed within the term "variant(s)" are chemically modified natural and synthetic KCNQ5 molecule. For example, variant may refer to polypeptides that differ from a reference polypeptide. Generally, the differences between the polypeptide that differs in amino acid sequence from reference polypeptide, and the reference polypeptide are limited so that the amino acid sequences of the reference and the variant are closely similar overall and, in some regions, identical. A variant and reference polypeptide may differ in amino acid sequence by one or more substitutions, deletions, additions, fusions and truncations that may be conservative or non-conservative and may be present in any combination. For example, variants may be those in which several, for instance from 50 to 30, from 30 to 20, from 20 to 10, from 10 to 5, from 5 to 3, from 3 to 2, from 2 to 1 amino acids are inserted, substituted, or deleted, in any combination. Additionally, a variant may be a fragment of a polypeptide that differs from a reference polypeptide sequence by being shorter than the reference sequence, such as by a terminal or internal deletion. A variant of a polypeptide also includes a polypeptide which retains essentially the same biological function or activity as such polypeptide, e.g., precursor proteins which can be activated by cleavage of the precursor portion to produce an active mature polypeptide. These variants may be allelic variations characterized by differences in the nucleotide sequences of the structural gene coding for the protein, or may involve differential splicing or post-translational modification. Variants also include a related protein having substantially the same biological activity, but obtained from a different species. The skilled artisan can produce variants having single or multiple amino acid substitutions, deletions, additions, or replacements. These variants may include, inter alia: (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more amino acids are deleted from the peptide or protein, or (iii) one in which one or more amino acids are added to the polypeptide or protein, or (iv) one in which one or more of the amino acid residues include a substitutent group, or (v) one in which the mature polypeptide is fused with another compound, such as a compound to increase the half-life of the polypeptide (for example, polyethylene glycol), or (vi) one in which the additional amino acids are fused to the mature polypeptide such as a leader or secretory sequence or a sequence which is employed for purification of the mature polypeptide or a precursor protein sequence. A variant of the polypeptide may also be a naturally occurring variant such as a naturally occurring allelic variant, or it may be a variant that is not known to occur naturally. All such variants defined above are deemed to be within the scope of teachings in the art.

The terms "vector", "cloning vector" and "expression vector" refer to the vehicle by which DNA can be introduced into a host cell, resulting in expression of the introduced sequence. An "intergeneric vector" is a vector that permits intergeneric conjugation, i.e., utilizes a system of passing DNA from *E. coli* to *Actinomycetes* directly. Intergeneric conjugation has fewer manipulations than transformation.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using standard molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Ausubel F M et al. (eds.), Current Protocols in Molecular Biology, John Wiley & Sons, Inc. (1994). Commonly used, commercially available vectors include, for example, pcDNA3 and pCR vectors from Invitrogen (Carlsbad, Calif.) and pGEM vectors from Promega (Madison, Wis.).

"Voltage-gated" activity or "voltage-gating" or "voltage dependence" refers to a characteristic of a potassium channel composed of individual polypeptide monomers or subunits. Generally, the probability of a voltage-gated potassium channel opening increases as a cell is depolarized. Voltage-gated potassium channels primarily allow efflux of potassium at membrane potentials more positive than the reversal potential for potassium ($E_K$) in typical cells, because they have greater probability of being open at such voltages. $E_K$ is the membrane potential at which there is no net flow of potassium ions because the electrical potential (i.e., voltage potential) driving potassium efflux is balanced by the concentration gradient for potassium. The membrane potential of cells depends primarily on their potassium channels and is typically between −60 and −100 mV for mammalian cells. This value is also known as the "reversal potential" or the "Nernst" potential for potassium. Some voltage-gated potassium channels undergo inactivation, which can reduce potassium efflux at higher membrane potentials. Potassium channels can also allow potassium influx in certain instances when they remain open at membrane potentials negative to $E_K$ (see, e.g., Adams and Nonner, in Potassium Channels, pp. 40-60 (Cook, ed., 1990)). The characteristic of voltage gating can be measured by a variety of techniques for measuring changes in current flow and ion flux through a channel, e.g., by changing the [$K^+$] of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

II. Isolated Polynucleotides Encoding rKCNQ5 or Portions Thereof

In practicing the methods disclosed herein, various agents can be used to modulate the activity and/or expression of rKCNQ5 in a cell. In one embodiment, an agent is a nucleic acid molecule encoding an rKCNQ5 polypeptide or a portion thereof. Such nucleic acid molecules are described in more detail below.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent because they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for an rKCNQ5 polypeptide (or a portion thereof) can be used to derive the rKCNQ5 amino acid sequence, using the genetic code to translate the DNA or RNA molecule into an amino acid sequence. Likewise, for any rKCNQ5 amino acid sequence, corresponding polynucleotide sequences that can encode rKCNQ5 protein can be deduced from the genetic code (which, because of its redundancy, will produce multiple polynucleotide sequences for any given amino acid sequence). Thus, description and/or disclosure herein of an rKCNQ5 polynucleotide sequence should be considered to also include description and/or disclosure of the amino acid sequence encoded by the polynucleotide sequence. Similarly, description and/or disclosure of an rKCNQ5 amino acid sequence herein should be considered to also include description and/or disclosure of all possible polynucleotide sequences that can encode the amino acid sequence. One aspect pertains to isolated nucleic acid molecules that encode rKCNQ5 proteins or biologically active portions thereof, as well as nucleic acid fragments sufficient for use as hybridization probes to identify rKCNQ5-encoding polynucleotides (e.g., rKCNQ5 mRNA) and fragments for use as PCR primers for the amplification or mutation of rKCNQ5 polynucleotides. Biologically active portions of KCNQ5 proteins include, for example, the six transmembrane domains, the pore region, and the conserved C-terminal region. It will be understood that, in discussing the uses of rKCNQ5 nucleic acid molecules, fragments of such polynucleotides as well as full length rKCNQ5 polynucleotides can be used.

A polynucleotide disclosed herein, e.g., having nucleotides 257-2008 of SEQ ID NO:1, or a portion thereof, can be isolated using standard molecular biology techniques and the sequence information provided herein. For example, using all or portion of the polynucleotide sequence of nucleotides 257-2008 of SEQ ID NO:1 as a hybridization probe, rKCNQ5 polynucleotides can be isolated using standard hybridization and cloning techniques (e.g., as described in Sambrook, J., Fritsh, E. F., and Maniatis, T. Molecular Cloning: A Laboratory Manual, 2nd ed., Cold Spring Harbor Laboratory, Cold Spring Harbor Laboratory Press, Cold Spring Harbor, N.Y., 1989).

Moreover, a polynucleotide encompassing all or a portion of nucleotides 257-2008 of SEQ ID NO:1 can be isolated by PCR using synthetic oligonucleotide primers designed based upon the sequence of, for example, SEQ ID NO:1.

A polynucleotide can be amplified using cDNA, mRNA or alternatively, genomic DNA, as a template and appropriate oligonucleotide primers according to standard PCR amplification techniques. The polynucleotide so amplified can be cloned into an appropriate vector and characterized by DNA sequence analysis. Furthermore, oligonucleotides corresponding to rKCNQ5 polynucleotide sequences can be prepared by standard synthetic techniques, e.g., using an automated DNA synthesizer.

In a preferred embodiment, an isolated polynucleotide comprises the polynucleotide sequence shown in nucleotides 257-2008 of SEQ ID NO:1.

In another preferred embodiment, an isolated polynucleotide comprises a polynucleotide which is a complement of the polynucleotide sequence shown in nucleotides 257-2008 of SEQ ID NO:1 or a portion of this polynucleotide sequence. A polynucleotide which is complementary to the polynucleotide sequence shown in nucleotides 257-2008 of SEQ ID NO:1 is one which is sufficiently complementary to the polynucleotide sequence shown in nucleotides 257-2008 of SEQ ID NO:1, such that it can hybridize to the polynucleotide sequence shown in nucleotides 257-2008 of SEQ ID NO:1, thereby forming a stable duplex.

In still another preferred embodiment, an isolated polynucleotide comprises a polynucleotide sequence which is at least about 95%, 98%, or more homologous to the polynucleotide sequence (e.g., to the entire length of the nucleotide sequence) shown in nucleotides 257-2008 of SEQ ID NO:1 or a portion of this nucleotide sequence.

Moreover, a polynucleotide can comprise only a portion of the polynucleotide sequence of nucleotides 257-2008 of SEQ ID NO:1; for example, a fragment which can be used as a probe or primer or a fragment encoding a biologically active portion of an rKCNQ5 protein. The polynucleotide sequence determined from the cloning of the rKCNQ5 gene allows for the generation of probes and primers designed for use in identifying and/or cloning other KCNQ family members, as well as KCNQ family homologues from other species. The probe/primer typically comprises a substantially purified oligonucleotide. In one embodiment, the oligonucleotide comprises a region of nucleotide sequence that hybridizes under stringent conditions to at least about 12 or 15, preferably about 20 or 25, more preferably about 30, 35, 40, 45, 50, 55, 60, 65, 75, or 100 consecutive polynucleotides of a sense sequence of nucleotides 257-2008 of SEQ ID NO:1 or of a naturally occurring allelic variant or mutant of nucleotides 257-2008 of SEQ ID NO:1. In another embodiment, a polynucleotide comprises a polynucleotide sequence which is at least about 100, 200, 300, 400, 500, 600, or 700 nucleotides in length and hybridizes under stringent hybridization conditions to a polynucleotides sequence of SEQ ID NO:1 or the complements thereof.

In another embodiment, a polynucleotide comprises at least about 100, 200, 300, 400, 500, 600, 700, or more contiguous nucleotides of SEQ ID NO:1.

In other embodiments, a polynucleotide has at least 95% identity, and more preferably 98% identity, with a polynucleotide comprising at least about 100, 200, 300, 400, 500, 600, 700, or more polynucleotides of SEQ ID NO:1.

Probes based on the rKCNQ5 polynucleotide sequence can be used to detect transcripts or genomic sequences encoding the same or homologous proteins. In preferred embodiments, the probe further comprises a label group attached thereto, for example, the label group can be a radioisotope, a fluorescent compound, an enzyme, or an enzyme co-factor. Such probes can be used as a part of a diagnostic test kit for identifying cells or tissues, particularly the brain, skeletal muscle, and the urinary bladder, which misexpress an rKCNQ5 protein, such as by measuring a level of an rKCNQ5-encoding polynucleotide in a sample of cells from a subject, for example, detecting rKCNQ5 mRNA levels or determining whether a genomic rKCNQ5 gene has been mutated or deleted.

A nucleic acid fragment encoding a "biologically active portion of an rKCNQ5 protein" can be prepared by isolating a portion of the polynucleotide sequence of nucleotides 257-2008 of SEQ ID NO:1 which encodes a polypeptide having an rKCNQ5 biological activity (i.e., the generation of voltage-dependent, slowly activating $K^+$-selective currents that are insensitive to the $K^+$ channel blocker TEA and display of a marked inward rectification at positive membrane voltages), expressing the encoded portion of the rKCNQ5 protein (e.g., by recombinant expression in vitro), and assessing the activity of the encoded portion of the rKCNQ5 protein.

Polynucleotides that differ from nucleotides 257-2008 of SEQ ID NO:1 due to degeneracy of the genetic code, and thus encode the same rKCNQ5 protein as that encoded by nucleotides 257-2008 of SEQ ID NO:1, are encompassed by the present disclosure. Accordingly, in another embodiment, an isolated polynucleotide has a polynucleotide sequence encoding a protein having an amino acid sequence shown in SEQ ID NO:2.

In addition to the rKCNQ5 polynucleotide sequence shown in nucleotides 257-2008 of SEQ ID NO:1, it will be appreciated by those skilled in the art that DNA sequence polymorphisms that lead to changes in the amino acid sequences of the rKCNQ5 protein may exist within a population. Such genetic polymorphism in the rKCNQ5 gene may exist among individuals within a population due to natural allelic variation. Such natural allelic variations include both functional and non-functional rKCNQ5 proteins and can typically result in 1-5% variance in the polynucleotide sequence of an rKCNQ5 gene. Any and all such polynucleotide variations and resulting amino acid polymorphisms in the rKCNQ5 gene that are the result of natural allelic variation and that do not alter the functional activity of an rKCNQ5 protein are intended to be within the scope of the present disclosure.

Nucleic acid molecules corresponding to natural allelic variants and homologues of the rKCNQ5 molecules can be isolated, for example, based on their homology to the rKCNQ5 polynucleotides disclosed herein using the cDNAs disclosed herein, or portions thereof, as a hybridization probe according to standard hybridization techniques. For example, an rKCNQ5 DNA can be isolated from a mouse or rat genomic DNA library using all or portion of SEQ ID NO:1 as a hybridization probe and standard hybridization techniques (e.g., as described in Sambrook, J., et al. Molecular Cloning: A Laboratory Manual, 2nd ed., Cold Spring Harbor Laboratory, Cold Spring Harbor, N.Y., 1989). Moreover, a polynucleotide encompassing all or a portion of a KCNQ5 gene can be isolated by the polymerase chain reaction using oligonucleotide primers designed based upon the sequence of SEQ ID NO:1. For example, mRNA can be isolated from cells (e.g., by the guanidinium-thiocyanate extraction procedure of Chirgwin et al., Biochemistry 18: 5294-99 (1979)) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the polynucleotide sequence shown in SEQ ID NO:1. A polynucleotide can be amplified using cDNA or, alternatively, genomic DNA, as a template and appropriate oligonucleotide primers according to standard PCR amplification techniques. The polynucleotide so amplified can be cloned into an appropriate vector and characterized by DNA sequence analysis. Furthermore, oligonucleotides corresponding to an rKCNQ5 polynucleotide sequence can be prepared by standard synthetic techniques, e.g., using an automated DNA synthesizer.

In another embodiment, an isolated polynucleotide can be identified based on shared nucleotide sequence identity using a mathematical algorithm. Such algorithms are outlined in more detail above (see, e.g., section 1).

In another embodiment, an isolated polynucleotide is at least 15, 20, 25, 30 or more polynucleotides in length and hybridizes under stringent conditions to the nucleic acid molecule comprising the nucleotide sequence of nucleotides 257-2008 of SEQ ID NO:1 or complements thereof. In other embodiment, the polynucleotide is at least 30, 50, 100, 150, 200, 250, 300, 350, 400, 450, 500, 550, or 600 nucleotides in length. Preferably, the conditions are such that sequences at least 95%, preferably at least about 98%, homologous to each other typically remain hybridized to each other. Preferably, an isolated nucleic acid molecule that hybridizes under stringent conditions to the sequence of nucleotides 257-2008 of SEQ ID NO:1 or complements thereof corresponds to a naturally-occurring nucleic acid molecule.

In addition to naturally-occurring allelic variants of rKCNQ5 sequences that may exist in the population, the skilled artisan will further appreciate that minor changes may be introduced by mutation into polynucleotide sequences, for example, of nucleotides 257-2008 of SEQ ID NO:1, thereby leading to changes in the amino acid sequence of the encoded protein, without altering the functional activity of an rKCNQ5 protein. For example, nucleotide substitutions leading to amino acid substitutions at "non-essential" amino acid residues may be made in the sequence of nucleotides 257-2008 of SEQ ID NO:1. A "non-essential" amino acid residue is a residue that can be altered from the wild-type sequence of an rKCNQ5 polynucleotide (e.g., the sequence of nucleotides 257-2008 of SEQ ID NO:1) without altering the functional activity of an rKCNQ5 molecule. Exemplary residues which are non-essential and, therefore, amenable to substitution can be identified by one of ordinary skill in the art by performing an amino acid alignment of rKCNQ5-related molecules and determining residues that are not conserved. Such residues, because they have not been conserved, are more likely amenable to substitution.

Accordingly, another aspect pertains to polynucleotides encoding rKCNQ5 proteins that contain changes in amino acid residues that are not essential for an rKCNQ5 activity.

Such rKCNQ5 proteins differ in amino acid sequence from SEQ ID NO:2 yet retain an inherent rKCNQ5 activity. An isolated polynucleotide encoding a non-natural variant of an rKCNQ5 protein can be created by introducing one or more nucleotide substitutions, additions, or deletions into the polynucleotide sequence of nucleotides 257-2008 of SEQ ID NO:1 such that one or more amino acid substitutions, additions, or deletions are introduced into the encoded protein. Mutations can be introduced into nucleotides 257-2008 of SEQ ID NO:1 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an rKCNQ5 polypeptide is preferably replaced with another amino acid residue from the same side chain family.

Alternatively, in another embodiment, mutations can be introduced randomly along all or part of an rKCNQ5 coding sequence, such as by saturation mutagenesis, and the resultant mutants can be screened for their ability, for example, to activate transcription, or to identify mutants that retain functional activity. Following mutagenesis, the rKCNQ5 mutant protein can be expressed recombinantly in a host cell and the functional activity of the mutant protein can be determined using assays available in the art for assessing KCNQ5 activity. The assays include, but are not limited to, patch clamp whole cell recording using mammalian cells as hosts or two-electrode voltage clamping using Xenopus laevis oocytes as hosts.

Yet another aspect pertains to isolated polynucleotides encoding rKCNQ5 fusion proteins. Such polynucleotides, comprising at least a first polynucleotide sequence encoding a full-length rKCNQ5 protein, polypeptide, or peptide having KCNQ5 activity operably linked to a second polynucleotide sequence encoding a non-rKCNQ5 protein, polypeptide, or peptide can be prepared by standard recombinant DNA techniques.

In a preferred embodiment, a mutant rKCNQ5 protein can be assayed for the ability to encode functional ion channels using electrophysiological methods as described above, for example patch clamp whole cell recording using mammalian cells as hosts or two-electrode voltage clamping using Xenopus laevis oocytes as hosts.

In addition to the polynucleotides encoding rKCNQ5 proteins described above, another aspect pertains to isolated polynucleotides which are antisense thereto. An "antisense" nucleic acid comprises a nucleotide sequence which is complementary to a "sense" nucleic acid encoding a protein, for example, complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire rKCNQ5 coding strand, or only to a portion thereof. In one embodiment, an antisense nucleic acid molecule is antisense to a "coding region" of the coding strand of a nucleotide sequence encoding rKCNQ5. The term "coding region" refers to the region of the nucleotide sequence comprising codons which are translated into amino acid residues. In another embodiment, the antisense polynucleotide is antisense to a "noncoding region" of the coding strand of a polynucleotide sequence encoding rKCNQ5. The term "noncoding region" refers to 5' and 3' sequences which flank the coding region that are not translated into amino acids (i.e., also referred to as 5' and 3' untranslated regions).

Given the coding strand sequences encoding rKCNQ5 disclosed herein, antisense nucleic acids can be designed according to the rules of Watson and Crick base pairing. The antisense polynucleotide can be complementary to the entire coding region of rKCNQ5 mRNA, but more preferably is an oligonucleotide which is antisense to only a portion of the coding or noncoding region of rKCNQ5 mRNA. For example, the antisense oligonucleotide can be complementary to the region surrounding the translation start site of rKCNQ5 mRNA. An antisense oligonucleotide can be, for example, about 5, 10, 15, 20, 25, 30, 35, 40, 45 or 50 nucleotides in length. An antisense polynucleotide can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, for example, phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense polynucleotides are typically administered to a subject or generated in situ such that they hybridize with or bind to cellular mRNA and/or genomic DNA encoding an rKCNQ5 protein to thereby inhibit expression of the protein, for example, by inhibiting transcription and/or translation. The hybridization can be by conventional nucleotide complementarity to form a stable duplex, or, for example, in the case of an antisense polynucleotide which binds to DNA duplexes, through specific interactions in the major groove of the double helix. An example of a route of administration of antisense polynucleotides include direct injection at a tissue site. Alternatively, antisense polynucleotides can be modified to target selected cells and then administered systemically. For example, for systemic administration, antisense molecules can be modified such that they specifically bind to receptors or antigens expressed on a selected cell surface, for example, by linking the antisense polynucleotides to peptides or antibodies which bind to cell surface receptors or antigens. The antisense polynucleotides can also be delivered to cells using the vectors described herein. To achieve sufficient intracellular concentrations of the antisense molecules, vector constructs in which the antisense polynucleotide is placed under the control of a strong pol II or pol III promoter are preferred.

In yet another embodiment, the antisense polynucleotide is an α-anomeric nucleic acid molecule. An α-anomeric nucleic acid molecule forms specific double-stranded hybrids with complementary RNA in which, contrary to the usual β-units, the strands run parallel to each other (Gaultier C et al., Nucleic Acids Res. 15:6625-41 (1987)). The antisense nucleic acid molecule can also comprise a 2'-o-methylribonucleotide (Inoue H et al., Nucleic Acids Res. 15:6131-48 (1987)), or a chimeric RNA-DNA analogue (Inoue H et al., FEBS Lett. 215:327-30 (1987)).

In still another embodiment, an antisense polynucleotide is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff J and Gerlach W L, Nature 334:585-91(1988))) can be used to catalytically cleave rKCNQ5 mRNA transcripts to thereby inhibit translation of rKCNQ5 mRNA. A ribozyme having specificity for an rKCNQ5-encoding nucleic acid can be designed based upon the nucleotide sequence of nucleotides 257-2008 of SEQ ID NO:1. For example, a derivative of a Tetrahymena L-19 IVS RNA can be constructed in which the nucleotide sequence of the active site is complementary to the nucleotide sequence to be cleaved in an rKCNQ5-encoding mRNA (see, e.g., U.S. Pat. Nos. 4,987,071 and 5,116,742). Alternatively, rKCNQ5 mRNA can be used to select a catalytic RNA having a specific ribonuclease activity from a pool of RNA molecules (see, e.g., Bartel D and Szostak J W, Science 261:1411-18 (1993)).

Alternatively, gene expression can be inhibited by targeting nucleotide sequences complementary to the regulatory region of rKCNQ5 (e.g., the rKCNQ5 promoter and/or enhancers) to form triple helical structures that prevent transcription of the rKCNQ5 gene in target cells (see generally, Helene C, Anticancer Drug Des. 6:569-84 (1991); Helene C et al., Ann. N.Y. Acad. Sci. 660:27-36 (1992); Maher L J, Bioassays 14:807-15 (1992)).

In yet another embodiment, the rKCNQ5 polynucleotides can be modified at the base moiety, sugar moiety, or phosphate backbone to improve, for example, the stability, hybridization, or solubility of the molecule. For example, the deoxyribose phosphate backbone of the polynucleotides can be modified to generate peptide nucleic acids (see Hyrup B et al., Bioorg. Med. Chem. 4:5-23 (1996)). As used herein, the terms "peptide nucleic acids" and "PNAs" refer to nucleic acid mimics, for example, DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B et al., supra; Perry-O'Keefe H et al., Proc. Natl. Acad. Sci. USA 93:14670-75 (1996).

PNAs of rKCNQ5 polynucleotides can be used in therapeutic and diagnostic applications. For example, PNAs can be used as antisense or antigene agents for sequence-specific modulation of gene expression by, for example, inducing transcription or translation arrest or inhibiting replication. PNAs of rKCNQ5 nucleic acid molecules can also be used in the analysis of single base pair mutations in a gene (e.g., by PNA-directed PCR clamping), as "artificial restriction enzymes" when used in combination with other enzymes, (e.g., S1 nucleases (Hyrup B et al., supra), or as probes or primers for DNA sequencing or hybridization (Hyrup B et al., supra; Perry-O'Keefe H et al., supra).

In another embodiment, PNAs of rKCNQ5 can be modified (e.g., to enhance their stability or cellular uptake) by attaching lipophilic or other helper groups to PNA, by the formation of PNA-DNA chimeras, or by the use of liposomes or other techniques of drug delivery known in the art. For example, PNA-DNA chimeras of rKCNQ5 polynucleotides can be generated which may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B et al., supra). The synthesis of PNA-DNA chimeras can be performed as described in Hyrup B et al., supra, and Finn P J et al., Nucleic Acids Res. 24:3357-63 (1996). For example, a DNA chain can be synthesized on a solid support using standard phosphoramidite coupling chemistry and modified nucleoside analogs, for example, 5'-(4-methoxytrityl)amino-5'-deoxythymidine phosphoramidite, can be used as a between the PNA and the 5' end of DNA (Mag M et al., Nucleic Acid Res. 17: 5973-88 (1989)). PNA monomers are then coupled in a stepwise manner to produce a chimeric molecule with a 5' PNA segment and a 3' DNA segment (Finn P J et al., supra). Alternatively, chimeric molecules can be synthesized with a 5' DNA segment and a 3' PNA segment (Petersen K H et al., Bioorg. Med. Chem. Lett. 5:1119-24 (1995)).

In other embodiments, the oligonucleotide may include other appended groups such as peptides (e.g., for targeting host cell receptors in vivo), or agents facilitating transport across the cell membrane (see, e.g., Letsinger R L et al., Proc. Natl. Acad. Sci. USA 86:6553-56 (1989); Lemaitre M et al., Proc. Natl. Acad. Sci. USA 84:648-52 (1987); PCT Publication No. WO88/09810) or the blood-brain barrier (see, e.g., PCT Publication No. WO89/10134). In addition, oligonucleotides can be modified with hybridization-triggered cleavage agents (see, e.g., van der Krol A R et al., Biotechniques 6:958-76 (1988)) or intercalating agents (see, e.g., Zon G, Pharm. Res. 5:539-49 (1988)). To this end, the oligonucleotide may be conjugated to another molecule, (e.g., a peptide, hybridization triggered cross-linking agent, transport agent, or hybridization-triggered cleavage agent).

In one embodiment, rKCNQ5 expression can be inhibited by short interfering RNAs (siRNA). The siRNA can be dsRNA having 19-25 nucleotides. siRNAs can be produced endogenously by degradation of longer dsRNA molecules by an RNase III-related nuclease called Dicer. siRNAs can also be introduced into a cell exogenously, or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 RNAs nucleotides with symmetric dinucleotide 3' overhangs. Using synthetic 21 bp siRNA duplexes (e.g., 19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer double-stranded RNAs (dsRNA), which may result in non-specific repression of translation of many proteins.

Second, siRNAs can be expressed in vivo from vectors. This approach can be used to stably express siRNAs in cells or transgenic animals. In one embodiment, siRNA expression vectors are engineered to drive siRNA transcription from polymerase III (pol III) transcription units. Pol III transcription units are suitable for hairpin siRNA expression because they deploy a short AT rich transcription termination site that leads to the addition of 2 bp overhangs (e.g., UU) to hairpin siRNAs—a feature that is helpful for siRNA function. The Pol III expression vectors can also be used to create transgenic mice that express siRNA.

In another embodiment, siRNAs can be expressed in a tissue-specific manner. Under this approach, long dsRNAs are first expressed from a promoter (such as CMV (pol II)) in the nuclei of selected cell lines or transgenic mice. The long dsRNAs are processed into siRNAs in the nuclei (e.g., by Dicer). The siRNAs exit from the nuclei and mediate gene-specific silencing. A similar approach can be used in conjunction with tissue-specific (pol II) promoters to create tissue-specific knockdown mice.

Any 3' dinucleotide overhang, such as UU, can be used for siRNA design. In some cases, G residues in the overhang are avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database (human, mouse, rat, etc.). Any target sequences with more than 16-17 contiguous base pairs of homology to other coding sequences may be eliminated from consideration in certain cases.

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see, e.g., Sui G et al., Proc. Natl. Acad. Sci. USA 99:5515-20 (2002)), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (see, e.g., Lee N S et al., Nature Biotechnol. 20:500-05 (2002)).

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene ilencing activities.

The length of nucleotide sequence being used as the stem of siRNA expression cassette can range, for instance, from 19 to 29. The loop size can range from 3 to 23 nucleotides. Other lengths and/or loop sizes can also be used.

In yet another embodiment, a 5' overhang in the hairpin siRNA construct can be used, provided that the hairpin siRNA is functional in gene silencing. In one specific example, the 5' overhang includes about 6 nucleotide residues.

In still yet another embodiment, the target sequence for RNAi is a 21-mer sequence fragment of nucleotides 257-2008 of SEQ ID NO:1. The 5' end of the target sequence has dinucleotide "NA," where "N" can be any base and "A" represents adenine. The remaining 19-mer sequence has a GC content of between 35% and 55%. In addition, the remaining 19-mer sequence does not include any four consecutive A or T (i.e., AAAA or TTTT), three consecutive G or C (i.e., GGG or CCC), or seven "GC" in a row.

Additional criteria can also be used for selecting RNAi target sequences. For instance, the GC content of the remaining 19-mer sequence can be limited to between 45% and 55%. Moreover, any 19-mer sequence having three consecutive identical bases (i.e., GGG, CCC, TTT, or AAA) or a palindrome sequence with 5 or more bases is excluded. Furthermore, the remaining 19-mer sequence can be selected to have low sequence homology to other genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. 19-mer sequences producing no hit to other human genes under the BLASTN search can be selected. During the search, the e-value may be set at a stringent value (such as "1").

The effectiveness of the siRNA sequences, as well as any other derived RNAi sequence, can be evaluated using various methods known in the art. For instance, an siRNA sequence can be introduced into a cell that expresses the rKCNQ5 gene. The polypeptide or mRNA level of the rKCNQ5 gene in the cell can be detected. A substantial change in the expression level of the rKCNQ5 gene before and after the introduction of the siRNA sequence is indicative of the effectiveness of the siRNA sequence in suppressing the expression of the rKCNQ5 gene. In one specific example, the expression levels of other genes are also monitored before and after the introduction of the siRNA sequence. An siRNA sequence which has inhibitory effect on rKCNQ5 gene expression but does not significantly affect the expression of other genes can be selected. In another specific example, multiple siRNA or other RNAi sequences can be introduced into the same target cell. These siRNA or RNAi sequences specifically inhibit rKCNQ5 gene expression but not the expression of other genes. In yet another specific example, siRNA or other RNAi sequences that inhibit the expression of the rKCNQ5 gene and other gene or genes can be used.

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

III. Isolated rKCNQ5 Proteins, Fragments Thereof, and Anti-rKCNQ5 Antibodies

Another aspect pertains to isolated rKCNQ5 proteins, and biologically active portions thereof, as well as polypeptide fragments suitable for use as immunogens to raise anti-rKCNQ5 antibodies. In one embodiment, native rKCNQ5 proteins can be isolated from cells or tissue sources by an appropriate purification scheme using standard protein purification techniques. In another embodiment, rKCNQ5 proteins are produced by recombinant DNA techniques. Alternative to recombinant expression, an rKCNQ5 protein or polypeptide can be synthesized chemically using standard peptide synthesis techniques. It will be understood that in discussing the uses of rKCNQ5 proteins, e.g., as shown in SEQ ID NO:2, that fragments of such proteins that are not full length rKCNQ5 polypeptides as well as full length rKCNQ5 proteins can be used.

Another aspect pertains to isolated rKCNQ5 proteins. Preferably, the rKCNQ5 proteins comprise the amino acid sequence encoded by nucleotides 257-2008 of SEQ ID NO:1 or a portion thereof. In another preferred embodiment, the protein comprises the amino acid sequence of SEQ ID NO:2 or a portion thereof. In other embodiments, the protein has at least at least 90%, more preferably 95%, and even more preferably 98% amino acid identity, with the amino acid sequence shown in SEQ ID NO:2 or a portion thereof. Preferred portions of rKCNQ5 polypeptide molecules are biologically active, for example, a portion of the KCNQ5 polypeptide having the ability to encode functional potassium-selective ion channels in a host system, for example mammalian cell lines or Xenopus laevis oocytes.

Biologically active portions of an rKCNQ5 protein include peptides comprising amino acid sequences sufficiently homologous to or derived from the amino acid sequence of the rKCNQ5 protein, which include less amino acids than the full length rKCNQ5 proteins, and exhibit at least one activity of an rKCNQ5 protein.

Also provided are rKCNQ5 chimeric or fusion proteins. For example, in one embodiment, the fusion protein is a GST-rKCNQ5 member fusion protein in which the rKCNQ5 member sequences are fused to the C-terminus of the GST sequences. In another embodiment, the fusion protein is an rKCNQ5-HA fusion protein in which the rKCNQ5 member nucleotide sequence is inserted in a vector such as pCEP4-HA vector (Herrscher R F et al., Genes Dev. 9:3067-82 (1995)) such that the rKCNQ5 member sequences are fused in frame to an influenza hemagglutinin epitope tag. Such fusion proteins can facilitate the purification of a recombinant rKCNQ5 member.

Fusion proteins and peptides produced by recombinant techniques may be secreted and isolated from a mixture of cells and medium containing the protein or peptide. Alternatively, the protein or peptide may be retained cytoplasmically and the cells harvested, lysed, and the protein isolated. A cell culture typically includes host cells, media, and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, an rKCNQ5 fusion protein is produced by standard recombinant DNA techniques. For example, DNA fragments coding for the different polypeptide sequences are ligated together in-frame in accordance with standard techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by standard techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide or an HA epitope tag). An rKCNQ5-encoding nucleic acid can be cloned into such an expression vector such that the fusion moiety is linked in-frame to the rKCNQ5 protein.

In another embodiment, the fusion protein is an rKCNQ5 protein containing a heterologous signal sequence at its N-terminus. In certain host cells (e.g., mammalian host cells), expression and/or secretion of rKCNQ5 can be increased through use of a heterologous signal sequence. The rKCNQ5 fusion proteins can be incorporated into pharmaceutical compositions and administered to a subject in vivo. Use of rKCNQ5 fusion proteins may be useful therapeutically for the treatment of disorders, for example, conditions related to infertility. Moreover, the rKCNQ5 fusion proteins can be used as immunogens to produce anti-rKCNQ5 antibodies in a subject.

As provided herein are functional potassium channels wherein at least one of the subunits of the functional channel is an rKCNQ5 protein or polypeptide described herein. KCNQ channels are known to form homodimers, heterodimers, homotetramers, and heterotetramers. For example, an rKCNQ5 protein can form a homodimer with itself, a heterodimer with a KCNQ5 protein from another species, a heterodimer with an rKCNQ5 protein variant, a heterodimer with KCNQ3, a homotetramer with 3 identical rKCNQ5 subunits, a heterotetramer with at least one different KCNQ5 subunit, or a heterotetramer with at least one different KCNQ protein, for example, KCNQ3.

Another aspect pertains to variants of the rKCNQ5 proteins which function as either rKCNQ5 agonists (mimetics) or as rKCNQ5 antagonists. Variants of the rKCNQ5 proteins can be generated by mutagenesis, for example, discrete point mutation or truncation of an rKCNQ5 protein. An agonist of the rKCNQ5 proteins can retain substantially the same, or a subset, of the biological activities of the naturally occurring form of an rKCNQ5 protein. An antagonist of an rKCNQ5 protein can inhibit one or more of the activities of the naturally occurring form of the rKCNQ5 protein by, for example, competitively modulating a cellular activity of an rKCNQ5 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the rKCNQ5 protein.

One embodiment pertains to derivatives of rKCNQ5 which may be formed by modifying at least one amino acid residue of rKCNQ5 by oxidation, reduction, or other derivatization processes known in the art.

In one embodiment, variants of an rKCNQ5 protein which function as either rKCNQ5 agonists (mimetics) or as rKCNQ5 antagonists can be identified by screening combinatorial libraries of mutants, for example, truncation mutants, of an rKCNQ5 protein for rKCNQ5 protein agonist or antagonist activity. In one embodiment, a variegated library of rKCNQ5 variants is generated by combinatorial mutagenesis at the nucleic acid level and is encoded by a variegated gene library. A variegated library of rKCNQ5 variants can be produced by, for example, enzymatically ligating a mixture of synthetic oligonucleotides into gene sequences such that a degenerate set of potential rKCNQ5 sequences is expressible as individual polypeptides, or alternatively, as a set of larger fusion proteins (e.g., for phage display) containing the set of rKCNQ5 sequences therein. There are a variety of methods which can be used to produce libraries of potential rKCNQ5 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential rKCNQ5 sequences. Methods for synthesizing degenerate oligonucleotides are known in the art (see, e.g., Narang S A, Tetrahedron 39:3-22 (1983); Itakura K et al., Annu. Rev. Biochem. 53:323-56 (1984); Itakura K et al., Science 198: 1056-63 (1977); Ike Y et al., Nucleic Acids Res. 11:477-88 (1983)).

In addition, libraries of fragments of an rKCNQ5 protein coding sequence can be used to generate a variegated population of rKCNQ5 fragments for screening and subsequent selection of variants of an rKCNQ5 protein. In one embodiment, a library of coding sequence fragments can be generated by treating a double stranded PCR fragment of an rKCNQ5 coding sequence with a nuclease under conditions wherein nicking occurs only about once per molecule, denaturing the double stranded DNA, renaturing the DNA to form double stranded DNA which can include sense\antisense pairs from different nicked products, removing single stranded portions from reformed duplexes by treatment with SI nuclease, and ligating the resulting fragment library into an expression vector. By this method, an expression library can be derived which encodes N-terminal, C-terminal, and internal fragments of various sizes of the rKCNQ5 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of rKCNQ5 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify rKCNQ5 variants (Arkin A P and Youvan D C, Proc. Natl. Acad. Sci. USA 89:7811-15 (1992); Delgrave S et al., Protein Eng. 6:327-31 (1993)).

In one embodiment, cell based assays can be exploited to analyze a variegated rKCNQ5 library. For example, a library of expression vectors can be transfected into a cell line which ordinarily synthesizes and secretes rKCNQ5. The transfected cells are then cultured such that rKCNQ5 and a particular mutant rKCNQ5 are secreted and the effect of expression of the mutant on rKCNQ5 activity in cell supernatants can be detected, for example, by any of a number of enzymatic assays. Plasmid DNA can then be recovered from the cells which score for inhibition, or alternatively, potentiation of rKCNQ5 activity, and the individual clones further characterized.

In addition to rKCNQ5 polypeptides consisting only of naturally-occurring amino acids, rKCNQ5 peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere J, Adv. Drug Res. 15:29 (1986); Veber D F and Freidinger R M, Trends Neurosci. 8:392-96 (1985); Evans B E et al., J. Med. Chem. 30:1229-39 (1987)) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as KCNQ5, but have one or more peptide linkages optionally replaced by a linkage selected from the group consisting of: —$CH_2NH$—, —$CH_2S$—, —$CH_2$—$CH_2$—, —CH=CH—(cis and trans), —$COCH_2$—, —CH(OH)$CH_2$—, and —CH2SO—, by methods known in the art and further described in the following references: Spatola A F in "Chemistry and Biochemistry of Amino Acids, Peptides, and Proteins," B. Weinstein, ed., Marcel Dekker, New York, p. 267 (1983); Spatola, A F, Vega Data (March 1983), Vol. 1, Issue 3, "Peptide Backbone Modifications" (general review); Morley J S, Trends Pharmcol. Sci. 1:463-68 (1980) (general review); Hudson D et al., Int. J. Pept. Prot. Res. 14:177-85 (1979) (—$CH_2NH$—, $CH_2CH_2$—); Spatola A F et al., Life Sci. 38:1243-49 (1986) (—$CH_2$—S); Hann M M, J. Chem. Soc. Perkin Trans. 1, 307-314 (1982) (—CH—CH—, cis and trans); Almquist R G et al., J. Med. Chem. 23:1392-98 (1980) (—$COCH_2$—); Jennings-White C et al., Tetrahedron Lett. 23:2533-34 (1982) (—$COCH_2$—); EP 0 045 665 (—CH(OH)$CH_2$—); Holladay M W et al., Tetrahedron Lett., 24:4401-04 (1983) (—C(OH) $CH_2$—); Hruby V J, Life Sci. 31:189-99 (1982) (—$CH_2$— S—). A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivatization (e.g., labeling) of peptidomimetics should not substantially interfere with the desired biological or pharmacological activity of the peptidomimetic.

Systematic substitution of one or more amino acids of an rKCNQ5 amino acid sequence with a D-amino acid of the same type (e.g., D-lysine in place of L-lysine) may be used to generate more stable peptides. In addition, constrained peptides comprising an rKCNQ5 amino acid sequence or a substantially identical sequence variation may be generated by methods known in the art (Rizo J and Gierasch L M, Ann. Rev. Biochem. 61:387-416 (1992)); for example, by adding internal cysteine residues capable of forming intramolecular disulfide bridges which cyclize the peptide.

The amino acid sequences of rKCNQ5 polypeptides identified herein will enable those of skill in the art to produce polypeptides corresponding to rKCNQ5 peptide sequences and sequence variants thereof. Such polypeptides may be produced in prokaryotic or eukaryotic host cells by expression of polynucleotides encoding an rKCNQ5 peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Gufte B and Merrifield R B, J. Am. Chem. Soc. 91:501-02 (1969); Chaiken I M, CRC Crit. Rev. Biochem. 11:255-301 (1981); Kaiser E T et al., Science 243:187-92 (1989); Merrifield B, Science 232:341-47 (1986); Kent S B H, Ann. Rev. Biochem. 57:957-89 (1988); Offord, R. E. (1980) Semisynthetic Proteins, Wiley Publishing.

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, may be incorporated into various embodiments. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides may be used therapeutically to treat disease.

An isolated rKCNQ5 protein, or a portion or fragment thereof, can also be used as an immunogen to generate antibodies that bind rKCNQ5 using standard techniques for polyclonal and monoclonal antibody preparation. A full-length rKCNQ5 protein can be used or, alternatively, the another aspect provides antigenic peptide fragments of rKCNQ5 for use as immunogens. The antigenic peptide of rKCNQ5 comprises at least 8 amino acid residues and encompasses an epitope of rKCNQ5 such that an antibody raised against the peptide forms a specific immune complex with rKCNQ5. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of an rKCNQ5 polypeptide that are located on the surface of the protein, for example, hydrophilic regions, and that are unique to an rKCNQ5 polypeptide. In one embodiment, such epitopes can be specific for an rKCNQ5 proteins from one species, such as rat or human (i.e., an antigenic peptide that spans a region of an rKCNQ5 polypeptide that is not conserved across species is used as immunogen; such non-conserved residues can be determined using an alignment such as that provided herein). A standard hydrophobicity analysis of the protein can be performed to identify hydrophilic regions.

An rKCNQ5 immunogen typically is used to prepare antibodies by immunizing a suitable subject (e.g., rabbit, goat, mouse, or other mammal) with the immunogen. An appropriate immunogenic preparation can contain, for example, a recombinantly expressed rKCNQ5 protein or a chemically synthesized rKCNQ5 peptide. The preparation can further include an adjuvant, such as Freund's complete or incomplete adjuvant, or similar immunostimulatory agent. Immunization of a suitable subject with an immunogenic rKCNQ5 preparation induces a polyclonal anti-rKCNQ5 antibody response.

Accordingly, another aspect pertains to the use of anti-rKCNQ5 antibodies. Polyclonal anti-rKCNQ5 antibodies can be prepared as described above by immunizing a suitable subject with an rKCNQ5 immunogen. The anti-rKCNQ5 antibody titer in the immunized subject can be monitored over time by standard techniques, such as with an enzyme linked immunosorbent assay (ELISA) using immobilized an rKCNQ5 polypeptide. If desired, the antibody molecules directed against an rKCNQ5 polypeptide can be isolated from the mammal (e.g., from the blood) and further purified by well known techniques, such as protein A chromatography to obtain the IgG fraction. At an appropriate time after immunization, for example, when the anti-rKCNQ5 antibody titers are highest, antibody-producing cells can be obtained from the subject and used to prepare monoclonal antibodies by standard techniques, such as the hybridoma technique originally described by Kohler G and Milstein C, Nature 256:495-97 (1975) (see also, Brown J P et al., J. Immunol. 127:539-46 (1981); Brown J P et al., J. Biol. Chem. 255:4980-83 (1980); Yeh M Y et al., Proc. Natl. Acad. Sci. USA 76:2927-31 (1979); Yeh M Y et al., Int. J. Cancer 29:269-75 (1982)), the more recent human B cell hybridoma technique (Kozbor D and Roder J C, Immunol. Today 4:72-79 (1983)), the EBV-hybridoma technique (Cole et al. (1985), Monoclonal Antibodies and Cancer Therapy, Alan R. Liss, Inc., pp. 77-96), or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); Lerner E A, Yale J. Biol. Med., 54:387-402 (1981); Gefter M L et al., Somatic Cell Genet. 3:231-36 (1977)). Briefly, an immortal cell line (typically a myeloma) is fused to lymphocytes (typically splenocytes) from a mammal immunized with an rKCNQ5 immunogen as described above, and the culture supernatants of the resulting hybridoma cells are screened to identify a hybridoma producing a monoclonal antibody that binds specifically to an rKCNQ5 polypeptide.

Any of the many well known protocols used for fusing lymphocytes and immortalized cell lines can be applied for the purpose of generating an anti-rKCNQ5 monoclonal antibody (see, e.g., Galfre G et al., Nature 266:550-52 (1977); Geifer M L et al., supra; Lerner E A, supra; Kenneth, Monoclonal Antibodies, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, for example, the P3-NS1/1-Ag-4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody are detected by screening the hybridoma culture supernatants for antibodies that bind an rKCNQ5 molecule, for example, using a standard ELISA assay.

As an alternative to preparing monoclonal antibody-secreting hybridomas, a monoclonal anti-rKCNQ5 antibody can be identified and isolated by screening a recombinant combinatorial immunoglobulin library (e.g., an antibody phage display library) with rKCNQ5 to thereby isolate immunoglobulin library members that bind an rKCNQ5 polypeptide. Kits for generating and screening phage display libraries are commercially available (e.g., the GE Healthcare Recombinant Phage Antibody System, Catalog No. 27-9400-01). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs P et al., Biotechnology (N.Y.) 9:1370-72 (1991); Hay B N et al., Hum. Antibodies Hybridomas 3:81-85 (1992); Huse W D et al., Science 246:1275-81 (1989); Griffiths A D et al., EMBO J. 12:725-34 (1993); Hawkins R E et al., J. Mol. Biol. 226:889-96 (1992); Clarkson T et al., Nature 352:624-28 (1991); Gram H et al., Proc. Natl. Acad. Sci. USA 89:3576-80 (1992); Garrard L J et al., Biotechnology (N.Y.) 9:1373-77 (1991); Hoogenboom H R et al., Nucleic Acids Res. 19:4133-37 (1991); Barbas C F et al., Proc. Natl. Acad. Sci. USA 88:7978-82 (1991); and McCafferty J et al., Nature 348:552-54 (1990).

Additionally, recombinant anti-rKCNQ5 antibodies, such as chimeric and humanized monoclonal antibodies, comprising both human and non-human portions, which can be made using standard recombinant DNA techniques, are within the scope of the present disclosure. Such chimeric and humanized monoclonal antibodies can be produced by recombinant DNA techniques known in the art, for example using methods described in WO 87/02671; EP 0 184 187; EP 0 171 496; EP 0 173 494; WO 86/01533; U.S. Pat. No. 4,816,567; EP 0 125 023; Better M et al., Science 240:1041-43 (1988); Liu A Y et al., Proc. Natl. Acad. Sci. USA 84:3439-43 (1987); Liu A Y et al., J. Immunol. 139:3521-26 (1987); Sun L K et al., Proc. Natl. Acad. Sci. USA 84:214-18 (1987); Nishimura Y et al., Cancer Res. 47:999-1005 (1987); Wood C R et al., Nature 314:446-49 (1985); Shaw D R et al., J. Natl. Cancer Inst. 80:1553-59 (1988); Morrison S L, Science 229:1202-07 (1985); U.S. Pat. No. 5,225,539; Verhocyan M et al., Science 239:1534-36 (1988); and Beidler C B et al., J. Immunol. 141:4053-60 (1988).

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable genetic display package and vectors containing nucleic acid molecules encoding a second polypeptide chain of a single binding pair member using techniques known in the art, for example, as described in U.S. Pat. Nos. 5,565,332; 5,871,907; or 5,733,743.

An anti-rKCNQ5 antibody (e.g., monoclonal antibody) can be used to isolate an rKCNQ5 polypeptide by standard techniques, such as affinity chromatography or immunoprecipitation. Anti-rKCNQ5 antibodies can facilitate the purification of natural rKCNQ5 polypeptides from cells and of recombinantly produced rKCNQ5 polypeptides expressed in host cells. Moreover, an anti-rKCNQ5 antibody can be used to detect an rKCNQ5 protein (e.g., in a cellular lysate or cell supernatant). Detection may be facilitated by coupling (i.e., physically linking) the antibody to a detectable substance. Accordingly, in one embodiment, an anti-rKCNQ5 antibody is labeled with a detectable substance. Examples of detectable substances include various enzymes, prosthetic groups, fluorescent materials, luminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, or phycoerythrin; an example of a luminescent material includes luminol; and examples of suitable radioactive material include $^{125}$I, $^{131}$I, $^{35}$S, or $^{3}$H.

Anti-rKCNQ5 antibodies are also obtainable by a process comprising:
  (a) immunizing an animal with an immunogenic rKCNQ5 protein, or an immunogenic portion thereof unique to an rKCNQ5 polypeptide; and
  (b) isolating from the animal antibodies that specifically bind to an rKCNQ5 protein.

Accordingly, in one embodiment, anti-rKCNQ5 antibodies can be used, e.g., intracellularly to inhibit protein activity. The use of intracellular antibodies to inhibit protein function in a cell is known in the art (see e.g., Carlson J R, Mol. Cell. Biol. 8:2638-46 (1988); Biocca S et al., EMBO J. 9:101-08 (1990); Werge T M et al., FEBS Lett. 274:193-98 (1990); Carlson J R, Proc. Natl. Acad. Sci. USA 90:7427-28 (1993); Marasco W A et al., Proc. Natl. Acad. Sci. USA 90:7889-93 (1993); Biocca S et al., Biotechnology (N.Y.) 12:396-99 (1994); Chen S-Y et al., Hum. Gene Ther. 5:595-601 (1994); Duan L et al., Proc. Natl. Acad. Sci. USA 91:5075-79 (1994); Chen S-Y et al., Proc. Natl. Acad. Sci. USA 91:5932-36 (1994); Beerli R R et al., J. Biol. Chem. 269:23931-36 (1994); Beerli R R et al., Biochem. Biophys. Res. Commun. 204:666-

72 (1994); Mhashilkar A M et al., EMBO J. 14:1542-51 (1995); Richardson J H et al., Proc. Natl. Acad. Sci. USA 92:3137-41 (1995); WO 94/02610; and WO 95/03832).

In one embodiment, a recombinant expression vector is prepared which encodes the antibody chains in a form such that, upon introduction of the vector into a cell, the antibody chains are expressed as a functional antibody in an intracellular compartment of the cell. For inhibition of rKCNQ5 activity according to the inhibitory methods disclosed herein, an intracellular antibody that specifically binds the rKCNQ5 protein is expressed in the cytoplasm of the cell. To prepare an intracellular antibody expression vector, antibody light and heavy chain cDNAs encoding antibody chains specific for the target protein of interest, for example, rKCNQ5, are isolated, typically from a hybridoma that secretes a monoclonal antibody specific for the rKCNQ5 protein. Hybridomas secreting anti-rKCNQ5 monoclonal antibodies, or recombinant anti-rKCNQ5 monoclonal antibodies, can be prepared as described above. Once a monoclonal antibody specific for rKCNQ5 protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat E A et al. (1991) Sequences of Proteins of Immunological Interest, Fifth Edition, U.S. Department of Health and Human Services, NIH Publication No. 91-3242 and in the "Vbase" human germlne sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit rKCNQ5 activity in a cell, the expression vector encoding the anti-rKCNQ5 intracellular antibody is introduced into the cell by standard transfection methods, as discussed herein.

IV. Recombinant Expression Vectors and Host Cells

Another aspect pertains to vectors, preferably expression vectors, containing a nucleic acid encoding an rKCNQ5 protein (or a portion thereof. The recombinant expression vectors comprise a nucleic acid in a form suitable for expression of the nucleic acid in a host cell, which means that the recombinant expression vectors include one or more regulatory sequences, selected on the basis of the host cells to be used for expression, which is operably linked to the nucleic acid sequence to be expressed. The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors can be introduced into host cells to thereby produce proteins or peptides, including fusion proteins or peptides, encoded by nucleic acids as described herein (e.g., rKCNQ5 proteins, mutant forms of rKCNQ5 proteins, fusion proteins, and the like).

The recombinant expression vectors can be designed for expression of rKCNQ5 proteins or protein fragments in prokaryotic or eukaryotic cells. For example, rKCNQ5 proteins can be expressed in bacterial cells such as *E. coli*, insect cells (using baculovirus expression vectors), yeast cells, or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase. Typical fusion expression vectors include, for example, pGEX (Pharmacia Biotech Inc; Smith D B and Johnson K S, Gene 67:3140 (1988)) and PMAL (New England Biolabs, Beverly, Mass.) which fuse glutathione S-transferase (GST) or maltose E binding protein, respectively, to the target recombinant protein.

Purified fusion proteins can be utilized, for example, in rKCNQ5 activity assays, (e.g., direct assays or competitive assays described in detail below), or to generate antibodies specific for rKCNQ5 proteins.

Examples of suitable inducible non-fusion *E. coli* expression vectors include pTrc (Amann E et al., Gene 69:301-15 (1988)) and pET 11d (Studier et al., Gene Expression Technology: Methods in Enzymology 185, Academic Press, San Diego, Calif. (1990) pp. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman S, Gene Expression Technology: Methods in Enzymology 185, Academic Press, San Diego, Calif. (1990) pp. 119-28). Another strategy is to alter the nucleic acid sequence of the nucleic acid to be inserted into an expression vector so that the individual codons for each amino acid are those preferentially utilized in E. coli (Wada K et al., Nucleic Acids Res. 20(Suppl.):2111-18 (1992)). Such alteration of nucleic acid sequences can be carried out by standard DNA synthesis techniques.

In another embodiment, the rKCNQ5 expression vector is a yeast expression vector. Examples of vectors for expression in yeast S. cerivisae include pYepSec1 (Baldari C et al., EMBO J. 6:229-34 (1987)), pMFa (Kurjan J and Herskowitz I, Cell 30:933-43 (1982)), pJRY 88 (Schultz L D et al., Gene 54:113-23 (1987)), pYES2 (Invitrogen Corporation, San Diego, Calif.), and picZ (Invitrogen Corp, San Diego, Calif.).

Alternatively, rKCNQ5 proteins or polypeptides can be expressed in insect cells using baculovirus expression vectors. Baculovirus vectors available for expression of proteins in cultured insect cells (e.g., Sf 9 cells) include the pAc series (Smith G E et al., Mol. Cell. Biol. 3:2156-65 (1983)) and the pVL series (Lucklow V A and Summers M D, Virology 170: 31-39 (1989)).

In yet another embodiment, a nucleic acid is expressed in mammalian cells using a mammalian expression vector. Examples of mammalian expression vectors include pCDM8 (Seed B, Nature 329:840-41 (1987)) and pMT2PC (Kaufman R J et al., EMBO J. 6:187-95 (1987)). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual, 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert C A et al., Genes Dev. 1:268-77 (1987)), lymphoid-specific promoters (Calame K and Eaton S, Adv. Immunol. 43:235-75 (1988)), in particular promoters of T cell receptors (Winoto A and Baltimore D, EMBO J. 8:729-33 (1989)) and immunoglobulins (Banerji J et al., Cell 33:729-40 (1983); Queen C and Baltimore D, Cell 33:741-48 (1983)), neuron-specific promoters (e.g., the neurofilament promoter; Byrne G W and Ruddle F H, Proc. Natl. Acad. Sci. USA 86:5473-77 (1989)), pancreas-specific promoters (Edlund T et al., Science 230:912-16 (1985)), and mammary gland-specific promoters (e.g., milk whey promoter; U.S. Pat. No. 4,873,316 and EP 0 264 166). Developmentally-regulated promoters are also encompassed, for example the murine hox promoters (Kessel M and Gruss P, Science 249:374-79 (1990)) and the α-fetoprotein promoter (Camper S A and Tilghman S M, Genes Dev. 3:537-46 (1989)).

Moreover, inducible regulatory systems for use in mammalian cells are known in the art, for example systems in which gene expression is regulated by heavy metal ions (see e.g., Mayo K E et al., Cell 29:99-108 (1982); Brinster R L et al., Nature 296:39-42 (1982); Searle P F et al., Mol. Cell. Biol. 5:1480-89 (1985)), heat shock (see e.g., Nouer L et al. (1991) in Heat Shock Response, ed. Nouer L, CRC, Boca Raton, Fla., pp. 167-220), hormones (see e.g., Lee F et al., Nature 294:228-32 (1981); Hynes N E et al., Proc. Natl. Acad. Sci. USA 78:2038-42 (1981); Klock G et al., Nature 329:734-36 (1987); Israel Dl and Kaufman R J, Nucleic Acids Res. 17:2589-2604 (1989); WO 93/23431), FK506-related molecules (see e.g., WO 94/18317) or tetracyclines (Gossen M and Bujard H, Proc. Natl. Acad. Sci. USA 89:5547-51 (1992); Gossen M et al., Science 268:1766-69 (1995); WO 94/29442; WO 96/01313). Accordingly, another embodiment provides a recombinant expression vector in which an rKCNQ5 DNA is operably linked to an inducible eukaryotic promoter, thereby allowing for inducible expression of an rKCNQ5 protein in eukaryotic cells.

Also known in the art are methods for expressing endogenous proteins using one-arm homologous recombination (see, e.g., U.S. Published Patent Application No. 2005/0003367; Zeh et al., Assay Drug Dev. Technol. 1:755-65 (2003); Qureshi et al., Assay Drug Dev. Technol. 1:767-76 (2003)). Briefly, an isolated genomic construct comprising a promoter operably linked to a KCNQ5 targeting sequence is introducing into a homogeneous population of cells (such as, for example, a homogeneous population of a human cell line or a homogenous population of Chinese hamster ovary (CHO) cells). The promoter is heterologous to the KCNQ5 target gene. Following recombination, the promoter controls transcription of an mRNA that encodes a KCNQ5 polypeptide. The population of cells is then incubated under conditions which cause expression of the KCNQ5 polypeptide.

A further aspect provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to rKCNQ5 mRNA. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub H et al., Trends Genet. 1:22-25 (1985).

Another aspect pertains to host cells into which a recombinant expression vector has been introduced. For example, an rKCNQ5 protein can be expressed in bacterial cells (such as, for example, E. coli), insect cells, yeast cells, or mammalian cells (such as, for example, CHO cells or COS cells). Other suitable host cells are known to those skilled in the art.

Vector DNA can be introduced into prokaryotic or eukaryotic cells via standard transformation or transfection techniques. As used herein, the terms "transformation" and "transfection" are intended to refer to a variety of art-recognized techniques for introducing foreign nucleic acid (e.g., DNA) into a host cell, including, for example, calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual, 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding an rKCNQ5 protein or can be introduced on a separate vector. Cells stably transfected with the introduced nucleic acid can be identified by drug selection (e.g., cells that have incorporated the selectable marker gene will survive, while the other cells die).

In the case of *Xenopus laevis* oocytes which are stably transfected with rKCNQ5, such lines can be made such that the rKCNQ5 gene is inducible. For example, the regulation of the expressed gene can be brought about by the double stable expression first of a "regulator" plasmid, which contains the tet-controlled transactivator (tTA) and a second "response" plasmid, which contains rKCNQ5, under the control of a promoter sequence that includes the tetracycline response element (TRE). The commercially available regulator plasmids are in vectors engineered for neomycin selection, necessitating that response vectors be constructed to include a second selectable marker. Using such methods, rKCNQ5 expression can be turned off in the presence of an agent, for example, tetracycline or a tetracycline-related compound (e.g., doxycycline) and turned on when the agent, for example, tetracycline, is not added to the culture medium. Construction of this type of cell line permits the stable expression of rKCNQ5 in cells in which it is normally toxic.

A host cell, such as a prokaryotic or eukaryotic host cell in culture, can be used to produce (i.e., express) an rKCNQ5 protein. Accordingly, a further aspect provides methods for producing an rKCNQ5 protein using the host cells. In one embodiment, the method comprises culturing the host cell (into which a recombinant expression vector encoding an rKCNQ5 protein has been introduced) in a suitable medium such that an rKCNQ5 protein is produced. In another embodiment, the method further comprises isolating an rKCNQ5 protein from the medium or the host cell.

Certain host cells can also be used to produce non-human transgenic animals. For example, in one embodiment, a host cell is a fertilized oocyte or an embryonic stem cell into which rKCNQ5-coding sequences have been introduced. Such host cells can then be used to create non-human transgenic animals in which exogenous rKCNQ5 sequences have been introduced into their genome or homologous recombinant animals in which endogenous rKCNQ5 sequences have been altered. Such animals are useful for studying the function and/or activity of an rKCNQ5 polypeptide and for identifying and/or evaluating modulators of rKCNQ5 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous rKCNQ5 gene has been altered by homologous recombination between the endogenous gene and an exogenous DNA molecule introduced into a cell of the animal, for example, an embryonic cell of the animal, prior to development of the animal.

A transgenic animal can be created by introducing an rKCNQ5-encoding nucleic acid into the male pronucleus of a fertilized oocyte, e.g., by microinjection, retroviral infection, and allowing the oocyte to develop in a pseudopregnant female foster animal. The rKCNQ5 sequence of SEQ ID NO:1 or portion thereof can be introduced as a transgene into the genome of a non-human animal. Alternatively, an rKCNQ5 gene homologue, such as another KCNQ family member, can be isolated based on hybridization to the rKCNQ5 family cDNA sequences of nucleotides 257-2008 of SEQ ID NO:1 (described further above) and used as a transgene.

Intronic sequences and polyadenylation signals can also be included in the transgene to increase the efficiency of expression of the transgene. A tissue-specific regulatory sequence(s) can be operably linked to an rKCNQ5 transgene to direct expression of an rKCNQ5 protein to particular cells. Methods for generating transgenic animals via embryo manipulation and microinjection, particularly animals such as mice, have become standard in the art and are described, for example, in U.S. Pat. Nos. 4,736,866; 4,870,009; 4,873,191; and in Hogan B, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of an rKCNQ5 transgene in its genome and/or expression of rKCNQ5 mRNA in tissues or cells of the animals. A transgenic founder animal can then be used to breed additional animals carrying the transgene. Moreover, transgenic animals carrying a transgene encoding an rKCNQ5 protein can further be bred to other transgenic animals carrying other transgenes.

To create a homologous recombinant animal, a vector is prepared which contains at least a portion of an rKCNQ5 gene into which a deletion, addition, or substitution has been introduced to thereby alter, for example, functionally disrupt, the rKCNQ5 gene. In a preferred embodiment, the vector is designed such that, upon homologous recombination, the endogenous rKCNQ5 gene is functionally disrupted (i.e., no longer encodes a functional protein; also referred to as a "knock out" vector). Alternatively, the vector can be designed such that, upon homologous recombination, the endogenous rKCNQ5 gene is mutated or otherwise altered but still encodes a functional protein (e.g., the upstream regulatory region can be altered to thereby alter the expression of the endogenous rKCNQ5 protein). In the homologous recombination vector, the altered portion of the rKCNQ5 gene is flanked at its 5' and 3' ends by additional nucleic acid sequence of the rKCNQ5 gene to allow for homologous recombination to occur between the exogenous rKCNQ5 gene carried by the vector and an endogenous rKCNQ5 gene in an embryonic stem cell. The additional flanking rKCNQ5 nucleic acid sequence is of sufficient length for successful homologous recombination with the endogenous gene. Typically, several kilobases of flanking DNA (both at the 5' and 3' ends) are included in the vector (see, e.g., Thomas K R and Capecchi M R, Cell 51:503-12 (1987) for a description of homologous recombination vectors). The vector is introduced into an embryonic stem cell line (e.g., by electroporation) and cells in which the introduced rKCNQ5 gene has homologously recombined with the endogenous rKCNQ5 gene are selected (see, e.g., Li E et al., Cell 69:915-26 (1992)). The selected cells are then injected into a blastocyst of an animal (e.g., a mouse) to form aggregation chimeras (see, e.g., Bradley A, Teratocarcinomas and Embryonic Stem Cells: A Practical Approach, Robertson E J, ed. (IRL, Oxford, 1987) pp. 113-152). A chimeric embryo can then be implanted into a suitable pseudopregnant female foster animal, and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in, for example, Bradley A, Curr. Opin. Biotechnol. 2:823-29 (1991); WO 90/11354; WO 91/01140; WO 92/0968; and WO 93/04169.

In addition to the foregoing, the skilled artisan will appreciate that other approaches known in the art for homologous recombination can be applied to the disclosure herein. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis W and Sauer B, Nucleic Acids Res. 21:2025-29 (1993); and Fukushige S and Sauer B, Proc. Natl. Acad. Sci. USA 89:7905-09 (1992)) and the FLP recombinase-FRT target system (e.g., as described in Dang DT and Perrimon N, Dev. Genet. 13:367-75 (1992); and Fiering S et al., Proc. Natl. Acad. Sci. USA 90:8469-73 (1993)). Tetracycline-regulated inducible homologous recombination systems, such as those described in WO 94/29442 and WO 96/01313, also can be used.

For example, in another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso M et al., Proc. Natl. Acad. Sci. USA 89:6232-36 (1992). Another example of a recombinase system is the FLP recombinase system of *Saccharomyces cerevisiae* (O'Gorman S et al., Science 251:1351-55 (1991)). If a cre/loxP recombinase system is used to regulate expression of the transgene, animals containing transgenes encoding both the Cre recombinase and a selected protein are required. Such animals can be provided through the construction of "double" transgenic animals, for example, by mating two transgenic animals, one containing a transgene encoding a selected protein and the other containing a transgene encoding a recombinase.

Clones of the non-human transgenic animals described herein can also be produced according to the methods described in, for example, Wilmut I et al., Nature 385:810-13 (1997); WO 97/07668; and WO 97/07669. In brief, a cell, for example, a somatic cell, from the transgenic animal can be isolated and induced to exit the growth cycle and enter $G_o$ phase. The quiescent cell can then be fused, for example, through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, for example, the somatic cell, is isolated.

V. Uses and Methods of the Invention

Ion channels are excellent targets for drugs. The polynucleotide encodes a novel rat voltage gated potassium channel, KCNQ5, modulators of which would be useful for identifying compounds for diagnosis, treatment, prevention or alleviation of diseases related to or adverse conditions of the central nervous system (CNS) and peripheral systems, including various types of pain such as, for example, somatic, cutaneous, or visceral pain caused by, for example burn, bruise, abrasion, laceration, broken bone, torn ligament, torn tendon, torn muscle, viral, bacterial, protozoal or fungal infection, contact dermatitis, inflammation (caused by, e.g., trauma, infection, surgery, burns, or diseases with an inflammatory component), cancer, toothache; neuropathic pain caused by, for example, injury to the central or peripheral nervous system due to cancer, HIV (human immunodeficiency virus) infection, tissue trauma, infection, autoimmune disease, diabetes, arthritis, diabetic neuropathy, trigeminal neuralgia, or drug administration; treating anxiety caused by, for example, panic disorder, generalized anxiety disorder, or stress disorder, particularly acute stress disorder, affective disorders, Alzheimer's disease, ataxia, CNS damage caused by trauma, stroke or neurodegenerative illness, cognitive deficits, compulsive behavior, dementia, depression, Huntington's disease, mania, memory impairment, memory disorders, memory dysfunction, motion disorders, motor disorders, age-related memory loss, neurodegenerative diseases, Parkinson's disease and Parkinson-like motor disorders, phobias, Pick's disease, psychosis, schizophrenia, spinal cord damage, tremor, seizures, convulsions, epilepsy, Stargardt-like macular dystrophy, cone-rod macular dystrophy, Salla disease, epilepsy, muscle relaxants, fever reducers, anxiolytics, antimigraine agents, analgesics, bipolar disorders, unipolar depression, functional bowel disorders (e.g., dyspepsia and irritable bowel syndrome), diarrhea, constipation, various types of urinary incontinence (e.g., urge urinary incontinence, stress urinary incontinence, overflow urinary incontinence or unconscious urinary incontinence, and mixed urinary incontinence), urinary urgency, bladder instability, neurogenic bladder, hearing loss, tinnitus, glaucoma, cognitive disorders, chronic inflammatory and neuralgic pain; for preventing and reducing drug dependence or tolerance for treatment of, for example, cancer, inflammation, ophthalmic diseases, and various CNS disorders.

The nucleic acid molecules, proteins, protein homologues, and antibodies described herein can be used in one or more of the following methods: a) methods of treatment, preferably in the CNS, skeletal muscle, or urinary bladder smooth muscle; b) screening assays; c) predictive medicine (e.g., diagnostic assays, prognostic assays, monitoring clinical trials, or pharmacogenetics). The isolated nucleic acid molecules can be used, for example, to express rKCNQ5 protein (e.g., via a recombinant expression vector in a host cell in gene therapy applications), to detect rKCNQ5 mRNA (e.g., in a biological sample) or a genetic alteration in an rKCNQ5 gene, and to modulate rKCNQ5 activity, as described further below. In addition, the rKCNQ5 proteins can be used to screen for naturally occurring rKCNQ5 binding proteins, to screen for drugs or compounds which modulate rKCNQ5 activity, as well as to treat disorders that would benefit from modulation of rKCNQ5, for example, characterized by insufficient or excessive production of rKCNQ5 protein or production of rKCNQ5 protein forms which have decreased or aberrant activity compared to rKCNQ5 wild type protein. Moreover, the anti-rKCNQ5 antibodies can be used to detect and isolate rKCNQ5 proteins, regulate the bioavailability of rKCNQ5 proteins, and modulate rKCNQ5 activity, for example, reduction of KCNQ5 activity in the brain will increase the neuronal excitability in the CNS. In preferred embodiments the methods disclosed herein, for example, detection, modulation of rKCNQ5, etc. are performed in the CNS, skeletal muscle, or urinary bladder smooth muscle.

A. Methods of Modulating KCNQ5

One aspect provides for methods of modulating rKCNQ5 in a cell, for example, for the purpose of identifying agents that modulate rKCNQ5 expression and/or activity, as well as both prophylactic and therapeutic methods of treating a subject at risk of (or susceptible to) a disorder or having a disorder associated with aberrant rKCNQ5 expression or activity or a disorder that would benefit from modulation of rKCNQ5 activity.

Yet another aspect pertains to methods of modulating rKCNQ5 expression and/or activity in a cell. The modulatory methods involve contacting the cell with an agent that modulates rKCNQ5 expression and/or activity such that rKCNQ5 expression and/or activity in the cell is modulated. The agent may act by modulating the activity of rKCNQ5 protein in the cell or by modulating transcription of the rKCNQ5 gene or translation of the rKCNQ5 mRNA.

Accordingly, in one embodiment, the agent inhibits rKCNQ5 activity. An inhibitory agent may function, for example, by directly inhibiting rKCNQ5 activity or by modulating a signaling pathway which negatively regulates rKCNQ5. In another embodiment, the agent stimulates rKCNQ5 activity. A stimulatory agent may function, for example, by directly stimulating rKCNQ5 activity, or by modulating a signaling pathway that leads to stimulation of rKCNQ5 activity. Exemplary inhibitory agents include antisense rKCNQ5 nucleic acid molecules (e.g., to inhibit translation of rKCNQ5 mRNA), intracellular anti-rKCNQ5 antibodies (e.g., to inhibit the activity of rKCNQ5 protein), and dominant negative mutants of the rKCNQ5 protein. Other inhibitory agents that can be used to inhibit the activity of an rKCNQ5 protein are chemical compounds that inhibit rKCNQ5 activity. Such compounds can be identified using screening assays that select for such compounds, as described herein. Additionally or alternatively, compounds that inhibit rKCNQ5 activity can be designed using approaches known in the art.

According to another modulatory method, rKCNQ5 activity is stimulated in a cell by contacting the cell with a stimulatory agent. Examples of such stimulatory agents include active rKCNQ5 protein and nucleic acid molecules encoding rKCNQ5 that are introduced into the cell to increase rKCNQ5 activity in the cell. A preferred stimulatory agent is a nucleic acid molecule encoding an rKCNQ5 protein, wherein the nucleic acid molecule is introduced into the cell in a form suitable for expression of the active rKCNQ5 protein in the cell. To express an rKCNQ5 protein in a cell, typically an rKCNQ5 cDNA is first introduced into a recombinant expression vector using standard molecular biology techniques, as described herein. An rKCNQ5 cDNA can be obtained, for example, by amplification using the PCR or by screening an appropriate cDNA library as described herein. Following isolation or amplification of rKCNQ5 cDNA, the DNA fragment is introduced into an expression vector and transfected into target cells by standard methods, as described herein. Other stimulatory agents that can be used to stimulate the activity and/or expression of an rKCNQ5 protein are chemical compounds that stimulate KCNQ5 activity and/or expression in cells, such as compounds that enhance KCNQ5 activity. Such compounds can be identified using screening assays that select for such compounds, as described in detail herein.

The modulatory methods can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (i.e., cultured) in vitro with a modulatory agent to modulate rKCNQ5 activity in the cells.

For stimulatory or inhibitory agents that comprise nucleic acids (including recombinant expression vectors encoding rKCNQ5 protein, antisense RNA, intracellular antibodies, or dominant negative inhibitors), the agents can be introduced into cells of the subject using methods known in the art for introducing nucleic acid (e.g., DNA) into cells in vivo. Examples of such methods encompass both non-viral and viral methods, including:

Direct Injection: Naked DNA can be introduced into cells in vivo by directly injecting the DNA into the cells (see, e.g., Acsadi G et al., Nature 332:815-18 (1991); Wolff J A et al., Science 247:1465-68 (1990)). For example, a delivery apparatus (e.g., a "gene gun") for injecting DNA into cells in vivo can be used. Such an apparatus is commercially available (e.g., from Bio-Rad Laboratories, Hercules, Calif.).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan J J et al., Gene Ther. 2:3849 (1995); San H et al., Hum. Gene Ther. 4:781-88 (1993)).

Receptor-Mediated DNA Uptake: Naked DNA can also be introduced into cells in vivo by complexing the DNA to a cation, such as polylysine, which is coupled to a ligand for a cell-surface receptor (see, e.g., Wu G Y and Wu C H, J. Biol. Chem. 263:14621-24 (1988); Wilson J M et at, J. Biol. Chem. 267:963-67 (1992); and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see, e.g., Curiel D T et al., Proc. Natl. Acad. Sci. USA 88:8850-54 (1991); Cristiano R J et al., Proc. Natl. Acad. Sci. USA 90:2122-26 (1993)).

Retroviruses: Defective retroviruses are well characterized for use in gene transfer for gene therapy purposes (for a review, see Miller A D, Blood 76:271-78 (1990)). A recombinant retrovirus can be constructed having a nucleotide sequence of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel F M et al. (eds.) Greene Publishing Associates, (1989), Sections 9.10-9.14 and other standard laboratory manuals. Examples of suitable retroviruses include pLJ, pZIP, pWE, and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see, e.g., Eglitis M A et al., Science 230:1395-98 (1985); Danos O and Mulligan R C, Proc. Natl. Acad. Sci. USA 85:6460-64 (1988); Wilson J M et al., Proc. Natl. Acad. Sci. USA 85:3014-18 (1988); Armentano D et al., Proc. Natl. Acad. Sci. USA 87:6141-45 (1990); Huber B E et al., Proc. Natl. Acad. Sci. USA 88:8039-43 (1991); Ferry N et al., Proc. Natl. Acad. Sci. USA 88:8377-81 (1991); Chowdhury J R et al., Science 254:1802-05 (1991); van Beusechem V W et al., Proc. Natl. Acad. Sci. USA 89:7640-44 (1992); Kay M A et al., Hum. Gene Ther. 3:641-47 (1992); Dai Y et al., Proc. Natl. Acad. Sci. USA 89:10892-95 (1992); Hwu P et al., J. Immunol. 150:4104-15 (1993); U.S. Pat. No. 4,868,116; U.S. Pat. No. 4,980,286; WO 89/07136; WO 89/02468; WO 89/05345; and WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle (see, e.g., Berkner K L, Biotechniques 6:616-29 (1988); Rosenfeld M A et al., Science 252:431-34 (1991); and Rosenfeld M A et al., Cell 68:143-55 (1992)). Suitable adenoviral vectors derived from the adenovirus strain Ad type 5 d1324 or other strains of adenovirus (e.g., Ad2, Ad3, Ad7, etc.) are well known to those skilled in the art. Recombinant adenoviruses are advantageous in that they do not require dividing cells to be effective gene delivery vehicles and can be used to infect a wide variety of cell types, including airway epithelium (Rosenfeld M A et al., Cell 68:143-55 (1992)), endothelial cells (Lemarchand P et al., Proc. Natl. Acad. Sci. USA 89:6482-86 (1992)), hepatocytes (Herz J and Gerard R D, Proc. Natl. Acad. Sci. USA 90:2812-16 (1993)), and muscle cells (Quantin B et al., Proc. Natl. Acad. Sci. USA 89:2581-84 (1992)). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner K L et al., supra; Haj-Ahmad Y and Graham F L, J. Virol. 57:267-74 (1986)). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle (for a review, see Muzyczka N, Curr. Top. Microbiol. Immunol. 158:97-129 (1992)). It is also one of the few viruses that may integrate its DNA into non-dividing cells, and exhibits a high frequency of stable integration (see, e.g., Flotte T R et al., Am. J. Respir. Cell. Mol. Biol. 7:349-56 (1992); Samulski R J et al., J. Virol. 63:3822-28 (1989); and McLaughlin S K et al., J. Virol. 62:1963-73 (1988)). Vectors containing as little as 300 base pairs of AAV can be packaged and can integrate. Space for exogenous DNA is limited to about 4.5 kb. An AAV vector such as that described in Tratschin J D et al., Mol. Cell. Biol. 5:3251-60 (1985), can be used to introduce DNA into cells. A variety of nucleic acids have been introduced into different cell types using AAV vectors (see, e.g., Hermonat P L and Muzyczka N, Proc. Natl. Acad. Sci. USA 81:6466-70 (1984); Tratschin J D et al., Mol. Cell. Biol. 4:2072-81 (1985); Wondisford F E et al., Mol. Endocrinol. 2:32-39 (1988); Tratschin J D et al., J. Virol. 51:611-19 (1984); and Flotte T R et al., J. Biol. Chem. 268:3781-90 (1993)).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection, or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

There are a variety of pathological conditions for which rKCNQ5 modulating agents can be used in treatment (see, e.g., section V, infra).

1. Prophylactic Methods

One aspect provides for a method for preventing in a subject, a disease or condition that would benefit from modulation of KCNQ5 activity and/or expression, e.g., a disorder associated with an aberrant KCNQ5 expression or activity (such as, e.g., urinary incontinence (see, e.g., U.S. Pat. No. 6,348,486, incorporated herein by reference) and neuropathic pain), by administering to the subject an rKCNQ5 polypeptide or an agent which modulates KCNQ5 polypeptide expression or at least one KCNQ5 activity. Subjects at risk for a disease which is caused or contributed to by aberrant KCNQ5 expression or activity can be identified by, for example, any or a combination of diagnostic or prognostic assays as described herein. Administration of a prophylactic agent can occur prior to the manifestation of symptoms characteristic of KCNQ5 aberrance, such that a disease or disorder is prevented or, alternatively, delayed in its progression. Depending on the type of KCNQ5 aberrance or condition, for example, an rKCNQ5 polypeptide, rKCNQ5 agonist, or rKCNQ5 antagonist agent can be used for treating the subject. The appropriate agent can be determined based on screening assays described herein.

2. Therapeutic Methods

Another aspect pertains to methods of modulating KCNQ5 expression or activity for therapeutic purposes. Accordingly, in an exemplary embodiment, the modulatory method involves contacting a cell with an rKCNQ5 polypeptide or agent that modulates one or more of the activities of KCNQ5 protein associated with the cell. An agent that modulates KCNQ5 protein activity can be an agent as described herein, such as a nucleic acid or a protein, a naturally-occurring target molecule of a KCNQ5 protein (e.g., a KCNQ5 binding protein), an rKCNQ5 antibody, an rKCNQ5 agonist or antagonist, a peptidomimetic of an rKCNQ5 agonist or antagonist, or other small molecule. In one embodiment, the agent stimulates one or more KCNQ5 activities. Examples of such stimulatory agents include active rKCNQ5 protein and a nucleic acid molecule encoding rKCNQ5 polypeptide that has been introduced into the cell. In another embodiment, the agent inhibits one or more KCNQ5 activities. Examples of such inhibitory agents include antisense rKCNQ5 nucleic acid molecules, anti-rKCNQ5 antibodies, and rKCNQ5 inhibitors. These modulatory methods can be performed in vitro (e.g., by culturing the cell with the agent) or, alternatively, in vivo (e.g., by administering the agent to a subject). As such, a further aspect provides methods of treating an individual afflicted with a disease or disorder that would benefit from modulation of a KCNQ5 protein (e.g., as described in section V, infra), or which is characterized by aberrant expression or activity of a KCNQ5 protein or nucleic acid molecule. In one embodiment, the method involves administering an agent (e.g., an agent identified by a screening assay described herein), or combination of agents that modulates (e.g., upregulates or downregulates) KCNQ5 expression or activity. In another embodiment, the method involves administering an rKCNQ5 protein or nucleic acid molecule as therapy to compensate for reduced or aberrant KCNQ5 expression or activity.

Stimulation of KCNQ5 activity is desirable in situations in which KCNQ5 is abnormally downregulated and/or in which increased KCNQ5 activity is likely to have a beneficial effect. Likewise, inhibition of KCNQ5 activity is desirable in situations in which KCNQ5 is abnormally upregulated and/or in which decreased KCNQ5 activity is likely to have a beneficial effect. Exemplary situations in which KCNQ5 modulation will be desirable are in the treatment of KCNQ5 associated disorders (see, e.g., section V, infra).

Agents identified by methods disclosed herein are useful for inducing, assisting or maintaining desirable bladder control in a mammal experiencing or susceptible to bladder instability or urinary incontinence. These methods include prevention, treatment or inhibition of bladder-related urinary conditions and bladder instability, including idiopathic bladder instability, nocturnal enuresis, nocturia, voiding dysfunction and urinary incontinence. Also treatable or preventable with the methods of this invention is bladder instability secondary to prostate hypertrophy. The agents identified by methods disclosed herein are also useful in promoting the temporary delay of urination whenever desirable. The agents may also be utilized to stabilize the bladder and treat or prevent incontinence which urge urinary incontinence, stress urinary incontinence or a combination of urge and stress incontinence in a mammal, which may also be referred to as mixed urge and stress incontinence. These methods include assistance in preventing or treating urinary incontinence associated with secondary conditions such as prostate hypertrophy.

These methods may be utilized to allow a recipient to control the urgency and frequency of urination. The methods of this invention include the treatment, prevention, inhibition and amelioration of urge urinary incontinence also known as bladder instability, neurogenic bladder, voiding dysfunction, hyperactive bladder, detrusor overactivity, detrusor hyperreflexia or uninhibited bladder.

As described above, useful methods include treatments, prevention, inhibition or amelioration of hyperactive or unstable bladder, neurogenic bladder, sensory bladder urgency, or hyperreflexic bladder. These uses include, but are not limited to, those for bladder activities and instabilities in which the urinary urgency is associated with prostatitis, prostatic hypertrophy, interstitial cystitis, urinary tract infections or vaginitis. The agents may also be used to assist in inhibition or correction of the conditions of Frequency-Urgency Syndrome, and lazy bladder, also known as infrequent voiding syndrome.

The agents may also be used to treat, prevent, inhibit, or limit the urinary incontinence, urinary instability or urinary urgency associated with or resulting from administrations of other medications, including diuretics, vasopressin antagonists, anticholinergic agents, sedatives or hypnotic agents, narcotics, alpha-adrenergic agonists, alpha-adrenergic antagonists, or calcium channel blockers.

The agents identified by methods disclosed herein can be useful for inducing or assisting in urinary bladder control or preventing or treating the maladies described herein in humans in need of such relief, including adult and pediatric uses. However, they may also be utilized for veterinary applications, particularly including canine and feline bladder control methods. If desired, the methods herein may also be used with farm animals, such as ovine, bovine, porcine and equine breeds.

B. Screening Assays

One aspect provides a method (also referred to herein as a "screening assay") for identifying modulators, that is, candidate or test compounds or agents (e.g., peptides, peptidomimetics, small molecules, or other drugs) which bind to rKCNQ5 proteins, have a stimulatory or inhibitory effect on, for example, rKCNQ5 expression or rKCNQ5 activity.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam K S, Anticancer Drug Des. 12:145-67 (1997)).

Examples of methods for the synthesis of molecular libraries can be found in the art, for example in: DeWitt S H et al., Proc. Natl. Acad. Sci. USA 90:6909-13 (1993); Erb E et al., Proc. Natl. Acad. Sci. USA 91:11422-26 (1994); Zuckermann R N et al., J. Med. Chem. 37:2678-85 (1994); Cho C Y et al., Science 261:1303-05 (1993); Carrell T et al., Angew. Chem. Int. Ed. Engl. 33:2059-61 (1994); Carrell T et al., Angew. Chem. Int. Ed. Engl. 33:2061-64 (1994); and Gallop M A et al., J. Med. Chem. 37:1233-51 (1994).

Libraries of compounds may be presented, for example, in solution (e.g., Houghten R A et al., Biotechniques 13:412-21 (1992)), or on beads (Lam K S et al., Nature 354:82-84 (1991)), chips (Fodor S P A et al., Nature 364:555-56 (1993)), bacteria (U.S. Pat. No. 5,223,409), spores (U.S. Pat. No. 5,223,409), plasmids (Cull M G et al., Proc. Natl. Acad. Sci. USA 89:1865-69 (1992)), or on phage (Scott J K and Smith G P, Science 249:386-90 (1990); Devlin J J et al., Science 249: 404-06 (1990); Cwirla S E et al., Proc. Natl. Acad. Sci. 87:6378-82 (1990); Felici F et al., J. Mol. Biol. 222:301-10 (1991); U.S. Pat. No. 5,223,409).

In many drug screening programs which test libraries of modulating agents and natural extracts, high throughput assays are desirable in order to maximize the number of modulating agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test modulating agent. Moreover, the effects of cellular toxicity and/or bioavailability of the test modulating agent can be generally ignored in the in vitro system, the assay instead being focused primarily on the effect of the drug on the molecular target as may be manifest in an alteration of binding affinity with upstream or downstream elements.

One embodiment provides assays for screening candidate or test compounds which bind to or modulate the activity of a KCNQ5 protein or polypeptide or biologically active portion thereof, for example, modulate the ability of KCNQ5 polypeptide to reduce neuronal excitability for anxiety and/or neuropathic pain, or to "quiet down" bladder smooth muscle activity for urinary incontinence. By "quiet down" is meant to suppress abnormal contractions of bladder smooth muscle cells in incontinence patients.

Assays can be used to screen for modulating agents, including rKCNQ5 homologs, which are either agonists or antagonists of the normal cellular function of the subject rKCNQ5 polypeptides. For example, one aspect provides a method in which an indicator composition is provided which has an rKCNQ5 protein having a KCNQ5 activity. The indicator composition can be contacted with a test compound. The effect of the test compound on KCNQ5 activity, as measured by a change in the indicator composition, can then be determined to thereby identify a compound that modulates the activity of a KCNQ5 protein. A statistically significant change, such as a decrease or increase, in the level of KCNQ5 activity in the presence of the test compound (relative to what is detected in the absence of the test compound) is indicative of the test compound being a KCNQ5 modulating agent. The indicator composition can be, for example, a cell or a cell extract.

The efficacy of the modulating agent can be assessed by generating dose response curves from data obtained using various concentrations of the test modulating agent. Moreover, a control assay can also be performed to provide a baseline for comparison. In the control assay, isolated and purified rKCNQ5 protein is added to a composition containing the KCNQ5-binding element, and the formation of a complex is quantitated in the absence of the test modulating agent.

In yet another embodiment, an assay is a cell-free assay in which an rKCNQ5 protein or biologically active portion thereof is contacted with a test compound and the ability of the test compound to bind to the rKCNQ5 protein or biologically active portion thereof is determined. Binding of the test compound to the rKCNQ5 protein can be determined either directly or indirectly as described above. In a preferred embodiment, the assay includes contacting the rKCNQ5 protein or biologically active portion thereof with a known compound which binds rKCNQ5 to form an assay mixture, contacting the assay mixture with a test compound, and determining the ability of the test compound to interact with an rKCNQ5 protein, wherein determining the ability of the test compound to interact with an rKCNQ5 protein comprises determining the ability of the test compound to preferentially bind to rKCNQ5 polypeptide or biologically active portion thereof as compared to the known compound.

In another embodiment, the assay is a cell-free assay in which an rKCNQ5 protein or biologically active portion thereof is contacted with a test compound and the ability of the test compound to modulate (e.g., stimulate or inhibit) the activity of the rKCNQ5 protein or biologically active portion thereof is determined. The rKCNQ5 protein can be provided as a lysate of cells that express rKCNQ5, as a purified or semipurified polypeptide, or as a recombinantly expressed polypeptide. In one embodiment, a cell-free assay system further comprises a cell extract or isolated components of a cell, such as mitochondria. Such cellular components can be isolated using techniques which are known in the art. Preferably, a cell free assay system further comprises at least one target molecule with which rKCNQ5 interacts, and the ability of the test compound to modulate the interaction of the rKCNQ5 with the target molecule(s) is monitored to thereby identify the test compound as a modulator of rKCNQ5 activity. Determining the ability of the test compound to modulate the activity of an rKCNQ5 protein can be accomplished, for example, by determining the ability of the rKCNQ5 protein to bind to an rKCNQ5 target molecule by one of the methods described above for determining direct binding. Determining the ability of the rKCNQ5 protein to bind to an rKCNQ5 target molecule can also be accomplished using a technology such as real-time Biomolecular Interaction Analysis (BIA) (see, e.g., Sjolander S and Urbaniczky C, Anal. Chem. 63:2338-45 (1991) and Szabo A et al., Curr. Opin. Struct. Biol. 5:699-705 (1995)). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting an rKCNQ5 protein or biologically active portion thereof with a known compound which binds the rKCNQ5 protein to form an assay mixture, contacting the assay mixture with a test compound, and determining the ability of the test compound to interact with the rKCNQ5 protein, wherein determining the ability of the test compound to interact with the rKCNQ5 protein comprises determining the ability of the rKCNQ5 protein to preferentially bind to or modulate the activity of an rKCNQ5 target molecule.

The cell-free assays are amenable to use of both soluble and/or membrane-bound forms of proteins (e.g., rKCNQ5 proteins or receptors having intracellular domains to which rKCNQ5 binds). In the case of cell-free assays in which a membrane-bound form a protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON® X-100 (polyoxyethylene octyl phenyl ether), TRITON® X-114 (octyphenol-polyethlene glycolether), THESIT® (dodecylpoly(ethyleneglycolether)$_n$, n=approx. 9), Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

An rKCNQ5 target molecule can be, for example, a protein. Suitable assays are known in the art that allow for the detection of protein-protein interactions (e.g., immunoprecipitations, two-hybrid assays, and the like). By performing such assays in the presence and absence of test compounds, these assays can be used to identify compounds that modulate (e.g., inhibit or enhance) the interaction of rKCNQ5 with a target molecule(s).

Determining the ability of the rKCNQ5 protein to bind to or interact with a ligand of an rKCNQ5 molecule can be accomplished, for example, by direct binding. In a direct binding assay, the rKCNQ5 protein could be coupled with a radioisotope or enzymatic label such that binding of the rKCNQ5 protein to an rKCNQ5 target molecule can be determined by detecting the labeled rKCNQ5 protein in a complex. For example, rKCNQ5 molecules, for example, rKCNQ5 proteins, can be labeled with, for example, $^{125}$I, $^{35}$S, $^{14}$C, or $^{3}$H, either directly or indirectly, and the radioisotope detected by direct counting of radioemission or by scintillation counting. Alternatively, rKCNQ5 molecules can be enzymatically labeled with, for example, horseradish peroxidase, alkaline phosphatase, or luciferase, and the enzymatic label detected by determination of conversion of an appropriate substrate to product.

Typically, it will be desirable to immobilize rKCNQ5 or its binding proteins to facilitate separation of complexes from uncomplexed forms of one or both of the proteins, as well as to accommodate automation of the assay. Binding of rKCNQ5 to an upstream or downstream binding element, in the presence and absence of a candidate agent, can be accomplished in any vessel suitable for containing the reactants. Examples include microtiter plates, test tubes, and microcentrifuge tubes. In one embodiment, a fusion protein can be provided which adds a domain that allows the protein to be bound to a matrix. For example, glutathione-S-transferase/rKCNQ5 (GST/rKCNQ5) fusion proteins can be adsorbed onto glutathione sepharose beads (Sigma Chemical, St. Louis, Mo.) or glutathione derivatized microtiter plates, which are then combined with the cell lysates and the test modulating agent, and the mixture incubated under conditions conducive to complex formation, for example, at physiological conditions for salt and pH, though slightly more stringent conditions may be desired. Following incubation, the beads are washed to remove any unbound label, and the matrix immobilized and radiolabel determined directly (e.g., beads placed in scintilant), or in the supernatant after the complexes are subsequently dissociated. Alternatively, the complexes can be dissociated from the matrix, separated by SDS-PAGE, and the level of rKCNQ5-binding protein found in the bead fraction quantitated from the gel using standard electrophoretic techniques.

Other techniques for immobilizing proteins on matrices are also available for use in the subject assay. For instance, rKCNQ5 or its cognate binding protein can be immobilized utilizing conjugation of biotin and streptavidin. For instance, biotinylated rKCNQ5 molecules can be prepared from biotin-NHS(N-hydroxy-succinimide) using techniques well known in the art (e.g., biotinylation kit, Pierce Biotechnology, Rockford, Ill.), and immobilized in the wells of streptavidin-coated 96 well plates (Pierce Biotechnology). Alternatively, antibodies reactive with rKCNQ5 but which do not interfere with binding of upstream or downstream elements can be derivatized to the wells of the plate, and rKCNQ5 trapped in the wells by antibody conjugation. As above, preparations of an rKCNQ5-binding protein (rKCNQ5-BP) and a test modulating agent are incubated in the rKCNQ5-presenting wells of the plate, and the amount of complex trapped in the well can be quantitated. Exemplary methods for detecting such complexes, in addition to those described above for the GST-immobilized complexes, include immunodetection of complexes using antibodies reactive with the rKCNQ5 binding element, or which are reactive with rKCNQ5 protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the rKCNQ5 binding protein. To illustrate, the rKCNQ5 binding protein can be chemically cross-linked or genetically fused with horseradish peroxidase, and the amount of protein trapped in the complex can be assessed with a chromogenic substrate of the enzyme, for example, 3,3'-diamino-benzadine terahydrochloride or 4-chloro-1-napthol. Likewise, a fusion protein comprising the protein and glutathione-5-transferase can be provided, and complex formation quantitated by detecting the GST activity using 1-chloro-2,4-dinitrobenzene (Habig W H et al., J. Biol. Chem. 249:7130-39 (1974)).

For processes which rely on immunodetection for quantitating one of the proteins trapped in the complex, antibodies against the protein, such as anti-rKCNQ5 antibodies, can be used. Alternatively, the protein to be detected in the complex can be "epitope tagged" in the form of a fusion protein which includes, in addition to the rKCNQ5 sequence, a second protein for which antibodies are readily available (e.g. from commercial sources). For instance, the GST fusion proteins described above can also be used for quantification of binding using antibodies against the GST moiety. Other useful epitope tags include myc-epitopes (see, e.g., Ellison M J and Hochstrasser M, J. Biol. Chem. 266:21150-57 (1991)) which includes a 10-residue sequence from c-myc, as well as the PFLAG® system (SigmaAldrich, St. Louis, Mo.) or the pEZZ-protein A system (GE Healthcare, Piscataway, N.J.).

It is also within the scope of the present disclosure to determine the ability of a compound to modulate the interaction between rKCNQ5 and their respective target molecules without the labeling of any of the interactants. For example, a microphysiometer can be used to detect the interaction of rKCNQ5 with their respective target molecules without the labeling of rKCNQ5 or the target molecules (see, e.g., McConnell H M et al., Science 257:1906-12 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In addition to cell-free assays, the readily available source of rKCNQ5 proteins also facilitates the generation of cell-based assays for identifying small molecule agonists/antagonists and the like. For example, cells can be caused to express or overexpress a recombinant rKCNQ5 protein in the presence and absence of a test modulating agent of interest, with the assay scoring for modulation in rKCNQ5 responses by the target cell mediated by the test agent. For example, as with the cell-free assays, modulating agents which produce a statistically significant change in rKCNQ5-dependent responses (either an increase or decrease) can be identified.

Recombinant expression vectors that can be used for expression of rKCNQ5 are known in the art (see discussions above). In one embodiment, within the expression vector the rKCNQ5-coding sequences are operably linked to regulatory sequences that allow for constitutive or inducible expression of rKCNQ5 in the indicator cell(s). Use of a recombinant expression vector that allows for constitutive or inducible expression of rKCNQ5 in a cell is preferred for identification of compounds that enhance or inhibit the activity of rKCNQ5. In an alternate embodiment, within the expression vector, the rKCNQ5 coding sequences are operably linked to regulatory sequences of the endogenous rKCNQ5 gene (i.e., the promoter regulatory region derived from the endogenous gene). Use of a recombinant expression vector in which rKCNQ5 expression is controlled by the endogenous regulatory sequences is preferred for identification of compounds that enhance or inhibit the transcriptional expression of rKCNQ5. In one embodiment, an assay is a cell-based assay comprising contacting a cell expressing a rKCNQ5 target molecule (e.g., a KCNQ5 intracellular interacting molecule) with a test compound and determining the ability of the test compound to modulate (e.g. stimulate or inhibit) the activity of the rKCNQ5 target molecule. Determining the ability of the test compound to modulate the activity of an rKCNQ5 target molecule can be accomplished, for example, by determining the ability of the rKCNQ5 protein to bind to or interact with the rKCNQ5 target molecule or its ligand.

In an illustrative embodiment, the expression or activity of rKCNQ5 is modulated in cells and the effects of modulating agents of interest on the readout of interest can be measured (such as, for example, the ion current magnitude can be measured electrophysiologically from *Xenopus laevis* oocytes expressing the said rKCNQ5 channels).

In another embodiment, modulators of rKCNQ5 expression are identified in a method wherein a cell is contacted with a candidate compound and the expression of rKCNQ5 mRNA or protein in the cell is determined. The level of expression of rKCNQ5 mRNA or protein in the presence of the candidate compound is compared to the level of expression of rKCNQ5 mRNA or protein in the absence of the candidate compound. The candidate compound can then be identified as a modulator of rKCNQ5 expression based on this comparison. For example, when expression of rKCNQ5 mRNA or protein is greater (e.g., statistically significantly greater) in the presence of the candidate compound than in its absence, the candidate compound is identified as a stimulator of rKCNQ5 mRNA or protein expression. Alternatively, when expression of rKCNQ5 mRNA or protein is less (e.g., statistically significantly less) in the presence of the candidate compound than in its absence, the candidate compound is identified as an inhibitor of rKCNQ5 mRNA or protein expression. The level of rKCNQ5 mRNA or protein expression in the cells can be determined by methods described herein for detecting rKCNQ5 mRNA or protein.

In a preferred embodiment, determining the ability of the rKCNQ5 protein to bind to or interact with an rKCNQ5 target molecule can be accomplished by measuring a read out of the activity of rKCNQ5 or of the target molecule. For example, the activity of rKCNQ5 or a target molecule can be determined by detecting induction of a cellular second messenger of the target, detecting catalytic/enzymatic activity of the target an appropriate substrate, detecting the induction of a reporter gene (comprising a target-responsive regulatory element operably linked to a nucleic acid encoding a detectable marker, e.g., chloramphenicol acetyl transferase), or detecting a target-regulated cellular response, for example, $Ca^{2+}$ influx induced by blocking of the rKCNQ5 channels.

In yet another aspect, rKCNQ5 proteins or portions thereof can be used as "bait proteins" in a two-hybrid assay or three-hybrid assay (see, e.g., U.S. Pat. No. 5,283,317; Zervos A S et al., Cell 72:223-32 (1993); Madura K et al., J. Biol. Chem. 268:12046-54 (1993); Bartel P et al., Biotechniques 14:920-24 (1993); Iwabuchi K et al., Oncogene 8:1693-96 (1993); and WO 94/10300) to identify other proteins which bind to or interact with rKCNQ5 and/or are involved in rKCNQ5 activity. Such KCNQ5-binding proteins are also likely to be involved in the propagation of signals by the KCNQ5 proteins or KCNQ5 targets as, for example, downstream elements of a KCNQ5-mediated signaling pathway. Alternatively, such rKCNQ5-binding proteins may be rKCNQ5 inhibitors.

The two-hybrid system is based on the modular nature of most transcription factors, which consist of separable DNA-binding and activation domains. Briefly, the assay utilizes two different DNA constructs. In one construct, the gene that codes for an rKCNQ5 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an rKCNQ5-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the rKCNQ5 protein.

In one aspect, the identified agents are novel analogs of known KCNQ channel blockers or activators. For example, in one embodiment, the identified agents are analogs of retigabine. In another exemplary embodiment, the identified agents are analogs of XE991.

A further aspect pertains to novel agents identified by the above-described screening assays. Accordingly, it is within the scope of the present disclosure to further use an agent identified as described herein in an appropriate animal model. For example, an agent identified as described herein (e.g., an rKCNQ5 modulating agent, an antisense rKCNQ5 polynucleotide, an rKCNQ5-specific antibody, or an rKCNQ5-binding partner) can be used in an animal model to determine the efficacy, toxicity, or side effects of treatment with such an agent. Alternatively, an agent identified as described herein can be used in an animal model to determine the mechanism of action of such an agent. Furthermore, another aspect pertains to uses of novel agents identified by the above-described screening assays for treatments as described herein.

In another embodiment, an rKCNQ5 promoter can be used in gain-of-function drug discovery applications via one-arm homologous recombination (see, e.g., U.S. Published Patent Application No. 2005/0003367; Zeh et al., Assay Drug Dev. Technol. 1:755-65 (2003); Qureshi et al., Assay Drug Dev. Technol. 1:767-76 (2003)). Briefly, an isolated genomic construct comprising an rKCNQ5 promoter operably linked to a targeting sequence is introducing into a homogeneous population of cells (such as, for example, a homogeneous population of a human cell line or a homogeneous population of CHO cells), wherein each of the cells comprises a signal transduction detection system. The term "targeting sequence" as used herein refers to a DNA sequence that is sufficiently homologous to a portion of the DNA sequence of a target gene to allow homologous recombination to occur within the cell. A sequence is sufficiently homologous if it is capable of binding to a target sequence under highly stringent conditions such as, for example, hybridization to filter bound DNA in 0.5 M $NaHPO_4$, 7% SDS, 1 mM EDTA at 65° C., and washing in 0.1×SSC/0.1% SDS at 68° C. The rKCNQ5 promoter is heterologous to the target gene. Following recombination, the promoter controls transcription of an mRNA that encodes a polypeptide comprising an activatable domain that can alter the signal detected from the signal transduction system. Incubating the population of cells under conditions which cause expression of the polypeptide and which cause activation of the activatable domain of the polypeptide allow selection of cells that have altered the signal detected from the signal transduction system.

In a preferred embodiment, the rKCNQ5 promoter comprises at least 100 contiguous nucleotides from nucleotides 1-256 of SEQ ID NO:1, more preferably at least 200 contiguous nucleotides from nucleotides 1-256 of SEQ ID NO:1, and even more preferably at least 250 contiguous nucleotides from nucleotides 1-256 of SEQ ID NO:1.

C. Methods of Rational Drug Design rKCNQ5 and rKCNQ5 binding polypeptides can be used for rational drug design of candidate KCNQ5-modulating agents. The rKCNQ5 polypeptides can be used for protein X-ray crystallography or other structure analysis methods, such as the DOCK program (see, e.g., Kuntz I D et al., J. Mol.

Biol. 161: 269-88 (1982); Kuntz I D, Science 257:1078-82 (1992)) and variants thereof. Potential therapeutic drugs may be designed rationally on the basis of structural information thus provided.

D. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample.

E. Predictive Medicine

Another aspect pertains to the field of predictive medicine in which diagnostic assays, prognostic assays, and monitoring clinical trials are used for prognostic (predictive) purposes to thereby treat an individual prophylactically. Accordingly, one aspect relates to diagnostic assays for determining rKCNQ5 protein and/or nucleic acid expression as well as KCNQ5 activity, in the context of a biological sample (e.g., blood, serum, cells, tissue (preferably the CNS, skeletal muscle, or urinary bladder smooth muscle)) to thereby determine whether an individual is afflicted with a disease or disorder, or is at risk of developing a disorder, associated with aberrant KCNQ5 expression or activity. A further aspect provides for prognostic (or predictive) assays for determining whether an individual is at risk of developing a disorder associated with KCNQ5 protein, nucleic acid expression, or activity. For example, mutations in a KCNQ5 gene can be assayed in a biological sample. Such assays can be used for prognostic or predictive purpose to thereby prophylactically treat an individual prior to the onset of a disorder characterized by or associated with KCNQ5 protein, nucleic acid expression, or activity.

Another aspect pertains to monitoring the influence of agents (e.g., drugs, compounds) on the expression or activity of KCNQ5 in clinical trials.

These and other agents are described in further detail in the following sections.

1. Diagnostic Assays

An exemplary method for detecting the presence or absence of KCNQ5 protein or nucleic acid in a biological sample involves obtaining a biological sample from a test subject and contacting the biological sample with a compound or an agent capable of detecting KCNQ5 protein or nucleic acid (e.g., mRNA, genomic DNA) that encodes KCNQ5 protein such that the presence of KCNQ5 protein or nucleic acid is detected in the biological sample. A preferred agent for detecting KCNQ5 mRNA or genomic DNA is a labeled nucleic acid probe capable of hybridizing to KCNQ5 mRNA or genomic DNA. The nucleic acid probe can be, for example, an rKCNQ5 nucleic acid, such as the nucleic acid of SEQ ID NO:1, or a portion thereof, such as an oligonucleotide of at least 15, 30, 50, 100, 250, 500 or more nucleotides in length and sufficient to specifically hybridize under stringent conditions to KCNQ5 mRNA or genomic DNA. Other suitable probes for use in the diagnostic assays are described herein.

A preferred agent for detecting KCNQ5 protein is an antibody capable of binding to KCNQ5 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells (preferably the CNS, skeletal muscle, or urinary bladder smooth muscle), and fluids present within a subject; that is, the detection method can be used to detect KCNQ5 mRNA, protein, or genomic DNA in a biological sample in vitro as well as in vivo. For example, in vitro techniques for detection of KCNQ5 mRNA include Northern hybridizations and in situ hybridizations. In vitro techniques for detection of KCNQ5 protein include enzyme linked immunosorbent assays (ELISAs), Western blots, immunoprecipitation, and immunofluorescence. In vitro techniques for detection of KCNQ5 genomic DNA include Southern hybridizations. Furthermore, in vivo techniques for detection of KCNQ5 protein include introducing into a subject a labeled anti-rKCNQ5 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a brain or urinary bladder sample isolated by standard means from a subject.

In another embodiment, the methods further involve obtaining a control biological sample from a control subject, contacting the control sample with a compound or agent capable of detecting KCNQ5 protein, mRNA, or genomic DNA, such that the presence of KCNQ5 protein, mRNA, or genomic DNA is detected in the biological sample, and comparing the presence of KCNQ5 protein, mRNA, or genomic DNA in the control sample with the presence of KCNQ5 protein, mRNA, or genomic DNA in the test sample.

An aspect also encompasses kits for detecting the presence of KCNQ5 in a biological sample. For example, the kit can comprise a labeled compound or agent capable of detecting KCNQ5 protein or mRNA in a biological sample; means for determining the amount of KCNQ5 in the sample; and means for comparing the amount of KCNQ5 in the sample with a standard. The compound or agent can be packaged in a suitable container. The kit can further comprise instructions for using the kit to detect KCNQ5 protein or nucleic acid.

2. Prognostic Assays

The diagnostic methods described herein can furthermore be utilized to identify subjects having or at risk of developing a disease or disorder associated with aberrant KCNQ5 expression or activity. For example, the assays described herein, such as the preceding diagnostic assays or the following assays, can be utilized to identify a subject having or at risk of developing a disorder associated with KCNQ5 protein, nucleic acid expression, or activity. Thus, a further aspect provides a method for identifying a disease or disorder associated with aberrant KCNQ5 expression or activity in which a test sample is obtained from a subject and KCNQ5 protein or nucleic acid (e.g., mRNA, genomic DNA) is detected, wherein the presence of KCNQ5 protein or nucleic acid is diagnostic for a subject having or at risk of developing a disease or disorder associated with aberrant KCNQ5 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant KCNQ5 expression or activity. Thus, another aspect provides methods for determining whether a subject can be effectively treated with an agent for a disorder associated with aberrant KCNQ5 expression or activity in which a test sample is obtained and KCNQ5 protein or nucleic acid expression or activity is detected (e.g., wherein the abundance of KCNQ5 protein or nucleic acid expression or activity is diagnostic for a subject that can be administered the agent to treat a disorder associated with aberrant KCNQ5 expression or activity).

The methods can also be used to detect genetic alterations in a KCNQ5 gene, thereby determining if a subject with the altered gene is at risk for a disorder associated with the KCNQ5 gene. In preferred embodiments, the methods include detecting, in a sample of cells from the subject, the presence or absence of a genetic alteration characterized by at least one of an alteration affecting the integrity of a gene encoding a KCNQ5 protein or the mls-expression of the KCNQ5 gene. For example, such genetic alterations can be detected by ascertaining the existence of at least one of 1) a deletion of one or more nucleotides from a KCNQ5 gene; 2) an addition of one or more nucleotides to a KCNQ5 gene; 3) a substitution of one or more nucleotides of a KCNQ5 gene, 4) a chromosomal rearrangement of a KCNQ5 gene; 5) an alteration in the level of a messenger RNA transcript of a KCNQ5 gene, 6) aberrant modification of a KCNQ5 gene, such as of the methylation pattern of the genomic DNA, 7) the presence of a non-wild type splicing pattern of a messenger RNA transcript of a KCNQ5 gene, 8) a non-wild type level of a KCNQ5 protein, 9) allelic loss of a KCNQ5 gene, and 10) inappropriate post-translational modification of a KCNQ5 protein. As described herein, there are a large number of assay techniques known in the art which can be used for detecting alterations in a KCNQ5 gene. A preferred biological sample is a tissue sample isolated by standard means from a subject, for example, a brain or urinary bladder sample.

In certain embodiments, detection of the alteration involves the use of a probe/primer in PCR (see, e.g., U.S. Pat. Nos. 4,683,195 and 4,683,202), such as anchor PCR or RACE PCR, or, alternatively, in a ligation chain reaction (LCR) (see, e.g., Landegren U et al., Science 241:1077-80 (1988); Nakazawa H et al., Proc. Natl. Acad. Sci. USA 91:360-64 (1994)), the latter of which can be particularly useful for detecting point mutations in the KCNQ5 gene (see, e.g., Abravaya K et al., Nucleic Acids Res. 23:675-82 (1995)). This method can include the steps of collecting a sample of cells from a patient, isolating nucleic acid (e.g., genomic, mRNA, or both) from the cells of the sample, contacting the nucleic acid sample with one or more primers which specifically hybridize to a KCNQ5 gene under conditions such that hybridization and amplification of the KCNQ5 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include, for example, self sustained sequence replication (Guatelli J C et al., Proc. Natl. Acad. Sci. USA 87:1874-78 (1990)), transcriptional amplification system (Kwoh D Y et al., Proc. Natl. Acad. Sci. USA 86:1173-77 (1989)), Q-Beta Replicase (Lizardi P M et al., Biotechnology (N.Y.) 6:1197 (1988)), or any other nucleic acid amplification method, followed by the detection of the amplified molecules using techniques well known to those of skill in the art. These detection schemes are especially useful for the detection of nucleic acid molecules if such molecules are present in very low numbers.

In an alternate embodiment, mutations in a KCNQ5 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in KCNQ5 can be identified by hybridizing a sample and control nucleic acids, e.g., DNA or RNA, to high density arrays containing hundreds or thousands of oligonucleotides probes (Cronin M T et al., Hum. Mutat. 7: 244-55 (1996); Kozal M J et al., Nat. Med. 2:753-59 (1996)). For example, genetic mutations in KCNQ5 can be identified in two dimensional arrays containing light-generated DNA probes as described in Cronin M T et al. (supra). Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the rKCNQ5 gene and detect mutations by comparing the sequence of the sample KCNQ5 with the corresponding wild-type (control) sequence. Examples of sequencing reactions include those based on techniques developed by Maxam A M and Gilbert W, Proc. Natl. Acad. Sci. USA 74:560-64 (1977) or Sanger F et al., Proc. Natl. Acad. Sci. USA 74:5463-67 (1977). It is also contemplated that any of a variety of automated sequencing procedures can be utilized when performing the diagnostic assays (see, e.g., Naeve C W et al., Biotechniques 19:448-53 (1995)), including sequencing by mass spectrometry (see, e.g., WO 94/16101; Cohen A S et al., Adv. Chromatogr. 36:127-62 (1996); and Griffin H G and Griffin A M, Appl. Biochem. Biotechnol. 38:147-59 (1993)).

Other methods for detecting mutations in the rKCNQ5 gene include methods in which protection from cleavage agents is used to detect mismatched bases in RNA/RNA or RNA/DNA heteroduplexes (Myers R M et al., Science 230: 1242-46 (1985)). In general, the art technique of "mismatch cleavage" starts by providing heteroduplexes formed by hybridizing (labeled)RNA or DNA containing the wild-type rKCNQ5 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation (see, e.g., Cotton R G H et al., Proc. Natl. Acad. Sci. USA 85:4397-4401 (1988); Saleeba J A and Cotton R G H, Meth. Enzymol. 217:286-95 (1993)). In a preferred embodiment, the control DNA or RNA can be labeled for detection. In still another embodiment, the mismatch cleavage reaction employs one or more proteins that recognize mismatched base pairs in double-stranded DNA (so called "DNA mismatch repair" enzymes) in defined systems for detecting and mapping point mutations in KCNQ5 obtained from samples of cells. For example, the mutY enzyme of E. coli cleaves A at G/A mismatches and the thymidine DNA glycosylase from HeLa cells cleaves T at G/T mismatches (Hsu I C et al., Carcinogenesis 15:1657-62 (1994)). According to an exemplary embodiment, a probe based on an rKCNQ5 sequence, for example, a wild-type rKCNQ5 sequence, is hybridized to a cDNA or other DNA product from a test cell(s). The duplex is treated with a DNA mismatch repair enzyme, and the cleavage products, if any, can be detected from electrophoresis protocols or the like (see, e.g., U.S. Pat. No. 5,459,039).

In other embodiments, alterations in electrophoretic mobility will be used to identify mutations in KCNQ5 genes. For example, single strand conformation polymorphism (SSCP) may be used to detect differences in electrophoretic mobility between mutant and wild type nucleic acids (Orita M et al., Proc Natl. Acad. Sci. USA: 86:2766-70 (1989); see also, Cotton R G H, Mutat. Res. 285:125-44 (1993); Hayashi K, Genet. Anal. Tech. Appl. 9:73-79 (1992)). Single-stranded DNA fragments of sample and control KCNQ5 nucleic acids will be denatured and allowed to renature. The secondary structure of single-stranded nucleic acids varies according to sequence; the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen J et al., Trends Genet. 7:5 (1991)).

In yet another embodiment, the movement of mutant or wild-type fragments in polyacrylamide gels containing a gradient of denaturant is assayed using denaturing gradient gel electrophoresis (DGGE) (Myers R M et al., Nature 313:495-98 (1985)). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum V and Riesner D, Biophys. Chem. 26:235-46 (1987)).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki R K et al., Nature 324:163-66 (1986); Saiki R K et al., Proc. Natl. Acad. Sci. USA 86:6230-34 (1989)). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the disclosed compositions and methods. Oligonucleotides used as primers for specific amplification may carry the mutation of interest in the center of the molecule (so that amplification depends on differential hybridization) (Gibbs R A et al., Nucleic Acids Res. 17:2437-48 (1989)) or at the extreme 3' end of one primer where, under appropriate conditions, mismatch can prevent, or reduce polymerase extension (Prosser J, Trends Biotechnol. 11:238-46 (1993)). In addition, it may be desirable to introduce a novel restriction site in the region of the mutation to create cleavage-based detection (Gasparini P et al., Mol. Cell. Probes 6:1-7 (1992)). It is anticipated that in certain embodiments amplification may also be performed using Taq ligase for amplification (Barany F, Proc. Natl. Acad. Sci. USA 88:189-93 (1991)). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, for example, in clinical settings to diagnose patients exhibiting symptoms or family history of a disease or illness involving a KCNQ5 gene.

Furthermore, any cell type or tissue in which KCNQ5 is expressed may be utilized in the prognostic assays described herein.

VI. Administration of KCNQ5 Modulating Agents

KCNQ5 modulating agents are administered to subjects in a biologically compatible form suitable for pharmaceutical administration in vivo to treat, for example, conditions described in section V, infra. By "biologically compatible form suitable for administration in vivo" is meant a form of the protein to be administered in which any toxic effects are outweighed by the therapeutic effects of the protein. The term subject is intended to include living organisms in which an immune response can be elicited, for example, mammals. Administration of an agent as described herein can be in any pharmacological form including a therapeutically active amount of an agent alone or in combination with a pharmaceutically acceptable carrier.

Administration of a therapeutically active amount of the therapeutic compositions is defined as an amount effective, at dosages and for periods of time necessary to achieve the desired result. For example, a therapeutically active amount of a KCNQ5 modulating agent may vary according to factors such as the disease state, age, sex, and weight of the individual, and the ability of peptide to elicit a desired response in the individual. Dosage regima may be adjusted to provide the optimum therapeutic response. For example, several divided doses may be administered daily, or the dose may be proportionally reduced as indicated by the exigencies of the therapeutic situation.

The therapeutic or pharmaceutical compositions can be administered by any suitable route known in the art including, for example, intravenous, subcutaneous, intramuscular, transdermal, intrathecal, or intracerebral or administration to cells in ex vivo treatment protocols. Administration can be either rapid as by injection or over a period of time as by slow infusion or administration of slow release formulation.

rKCNQ5 can also be linked or conjugated with agents that provide desirable pharmaceutical or pharmacodynamic properties. For example, rKCNQ5 can be coupled to any substance known in the art to promote penetration or transport across the blood-brain barrier such as an antibody to the transferrin receptor, and administered by intravenous injection (see, e.g., Friden P M et al., Science 259:373-77 (1993)). Furthermore, KCNQ5 can be stably linked to a polymer such as polyethylene glycol to obtain desirable properties of solubility, stability, half-life, and other pharmaceutically advantageous properties (see, e.g., Davis et al., Enzyme Eng. 4:169-73 (1978); Burnham N L, Am. J. Hosp. Pharm. 51:210-18 (1994)).

Furthermore, the rKCNQ5 polypeptide can be in a composition which aids in delivery into the cytosol of a cell. For example, the peptide may be conjugated with a carrier moiety such as a liposome that is capable of delivering the peptide into the cytosol of a cell. Such methods are well known in the art (see, e.g., Amselem S et al., Chem. Phys. Lipids 64:219-37 (1993)). Alternatively, the rKCNQ5 polypeptide can be modified to include specific transit peptides or fused to such transit peptides which are capable of delivering their KCNQ5 polypeptide into a cell. In addition, the polypeptide can be delivered directly into a cell by microinjection.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any standard media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. rKCNQ5 can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used.

It is also provided that certain formulations containing the rKCNQ5 polypeptide or fragment thereof are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents, or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such compounds can be determined by standard pharmaceutical procedures in cell cultures or experimental animals, for example, for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods disclosed herein, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment, an rKCNQ5 polypeptide may be therapeutically administered by implanting into patients vectors or cells capable of producing a biologically-active form of rKCNQ5 or a precursor of rKCNQ5, that is, a molecule that can be readily converted to a biological-active form of rKCNQ5 by the body.

In one approach, cells that secrete rKCNQ5 may be encapsulated into semipermeable membranes for implantation into a patient. The cells can be cells that normally express rKCNQ5 or a precursor thereof or the cells can be transformed to express rKCNQ5 or a biologically active fragment thereof or a precursor thereof. It is preferred that the cell be of human origin. However, the formulations and methods herein can be used for veterinary as well as human applications and the term "patient" or "subject" as used herein is intended to include human and veterinary patients.

Monitoring the influence of agents (e.g., drugs or compounds) on the expression or activity of an rKCNQ5 protein can be applied not only in basic drug screening, but also in clinical trials. For example, the effectiveness of an agent determined by a screening assay as described herein to increase KCNQ5 gene expression, protein levels, or upregulate KCNQ5 activity, can be monitored in clinical trials of subjects exhibiting decreased KCNQ5 gene expression, protein levels, or downregulated KCNQ5 activity. Alternatively, the effectiveness of an agent determined by a screening assay to decrease KCNQ5 gene expression, protein levels, or downregulate KCNQ5 activity, can be monitored in clinical trials of subjects exhibiting increased KCNQ5 gene expression, protein levels, or upregulated KCNQ5 activity. In such clinical trials, the expression or activity of a KCNQ5 gene, and preferably, other genes that have been implicated in a disorder can be used as a "read out" or markers of the phenotype of a particular cell.

For example, and not by way of limitation, genes, including KCNQ5, that are modulated in cells by treatment with an agent (e.g., compound, drug, or small molecule) which modulates KCNQ5 activity (e.g., identified in a screening assay as described herein) can be identified. Thus, to study the effect of agents on a KCNQ5 associated disorder, for example, in a clinical trial, cells can be isolated and RNA prepared and analyzed for the levels of expression of KCNQ5 and other genes implicated in the KCNQ5 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of KCNQ5 or other genes. In this way, the gene expression pattern can serve as a marker, indicative of the physiological response of the cells to the agent. Accordingly, this response state may be determined before, and at various points during treatment of the individual with the agent.

A preferred embodiment provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a KCNQ5 protein, mRNA, or genomic DNA in the pre-administration sample; (iii) obtaining one or more post-administration samples from the subject; (iv) detecting the level of expression or activity of the KCNQ5 protein, mRNA, or genomic DNA in the post-administration samples; (v) comparing the level of expression or activity of the KCNQ5 protein, mRNA, or genomic DNA in the pre-administration sample with the KCNQ5 protein, mRNA, or genomic DNA in the post administration sample or samples; and (vi) altering the administration of the agent to the subject accordingly. For example, increased administration of the agent may be desirable to increase the expression or activity of KCNQ5 to higher levels than detected, that is, to increase the effectiveness of the agent. Alternatively, decreased administration of the agent may be desirable to decrease expression or activity of KCNQ5 to lower levels than detected, that is, to decrease the effectiveness of the agent. According to such an embodiment, KCNQ5 expression or activity may be used as an indicator of the effectiveness of an agent, even in the absence of an observable phenotypic response.

In a preferred embodiment, the ability of a KCNQ5 modulating agent to modulate, for example, conditions described in section V (infra) in a subject that would benefit from modulation of the expression and/or activity of KCNQ5 can be measured by detecting an improvement in the condition of the patient after the administration of the agent. Such improvement can be readily measured by one of ordinary skill in the art using indicators appropriate for the specific condition of the patient. Monitoring the response of the patient by measuring changes in the condition of the patient is preferred in situations were the collection of biopsy materials would pose an increased risk and/or detriment to the patient.

It is likely that the level of KCNQ5 may be altered in a variety of conditions and that quantification of KCNQ5 levels would provide clinically useful information.

Furthermore, in the treatment of disease conditions, compositions containing rKCNQ5 can be administered exogenously and it would likely be desirable to achieve certain target levels of rKCNQ5 polypeptide in sera, in any desired tissue compartment, or in the affected tissue. It would, therefore, be advantageous to be able to monitor the levels of rKCNQ5 polypeptide in a patient or in a biological sample including a tissue biopsy sample obtained from a patient and, in some cases, also monitoring the levels of native KCNQ5. Accordingly, another aspect provides methods for detecting the presence of KCNQ5 in a sample from a patient.

VII. Kits of the Invention

Another aspect pertains to kits for carrying out the screening assays, modulatory methods, or diagnostic assays. For example, a kit for carrying out a screening assay can include a cell comprising an rKCNQ5 polypeptide, means for determining rKCNQ5 polypeptide activity, and instructions for using the kit to identify modulators of rKCNQ5 activity. In another embodiment, a kit for carrying out a screening assay can include an composition comprising an rKCNQ5 polypeptide, means for determining rKCNQ5 activity, and instructions for using the kit to identify modulators of rKCNQ5 activity.

Another embodiment provides a kit for carrying out a modulatory method. The kit can include, for example, a modulatory agent (e.g., an rKCNQ5 inhibitory or stimulatory agent) in a suitable carrier and packaged in a suitable container with instructions for use of the modulator to modulate rKCNQ5 activity.

Another aspect pertains to a kit for diagnosing a disorder associated with aberrant KCNQ5 expression and/or activity in a subject. The kit can include a reagent for determining expression of KCNQ5 (e.g., a nucleic acid probe(s) for detecting KCNQ5 mRNA or one or more antibodies for detection of KCNQ5 proteins), a control to which the results of the subject are compared, and instructions for using the kit for diagnostic purposes.

The practice of the methods disclosed herein will employ, unless otherwise indicated, standard techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

The disclosure herein is further defined in the following Examples. It should be understood that these Examples, while indicating preferred embodiments, are given by way of illustration only. From the above discussion and these Examples, one skilled in the art can ascertain the preferred features, and without departing from the spirit and scope thereof, can make various changes and modifications to adapt it to various uses and conditions.

Example 1

Sequencing of rKCNQ5

Human KCNQ5 sequence (GenBank Accession number AF249278) was used in the Basic Local Alignment Search Tool (BLASTn) to search the National Center for Biotechnology Information (NCBI) expressed sequence tag (EST) database. Four (4) rat ESTs were identified from the NCBI database, GenBank Accession numbers BE103175, BI290441, BF523361, and AC095904, spanning the entire hKCNQ5 open reading frame with 2 gaps. To fill the gaps, two sets of primers were made according to the rat EST sequences for reverse transcription polymerase chain reaction (RT-PCR). Primers were synthesized in house using the ABI 3948 Nucleic acid synthesis and purification system.

In order to fill the gaps, the primers utilized were: AAGC-CGCTCTCCTACACCA (first gap, forward; SEQ ID NO:3), GAGAGCAATCTTCCCAGCC (first gap, reverse; SEQ ID NO:4), TGGCTGGGAAGATTGCTCTC (second gap, forward; SEQ ID NO:5), CTCAGCAGTGATGTCAGTG (second gap, reverse; SEQ ID NO:6). For PCR, 1 µl of 10 µM primers were used. RT-PCR was done using these primers, and the PCR products were sequenced to obtain the missing sequence information or gap.

Example 2

PCR Cloning

Total RNA was isolated from rat brain by TRIZOL ® reagent (monophasic solution of phenol and guanidine isothiocyanate; Invitrogen, Carlsbad, Calif.) as directed by the manufacturer. Brain tissue was homogenized in 1 ml of TRIZOL ® solution. 200 µl of chloroform was added. Mix the solution by shaking the microcentrifuge tube vigorously, and incubate at room temperature for 1 min. Spin the tube in a table top centrifuge at 13000 rpm (18000×g) at 4° C. for 10 min. Transfer the upper phase to a fresh tube, and add equal volume of isopropyl alcohol. Incubate at room temperature for 10 min, and centrifuge for 10 min at 13000 rpm at 4° C. RNA pellets were resuspended in water. These techniques are well known in the art. The total RNA was used for all polymerase chain reactions (PCR).

All RT-PCR were performed using the one-step RT-PCR kit from Invitrogen, as directed by the manufacturer. In a tube, mix 25 µl of 2× reaction buffer, 0.5 µg RNA, 1 µl each of 10 µM primers, 1 µl of RT/Platinum Taq mix, and water to a total of 50 µl. Reaction was done using a DNA thermocycler 9600 (Perkin Elmer, Boston, Mass.) at: 1 cycle of: 50° C., 30 min; 95° C., 2 min, and 40 cycles of: 95° C., 30 sec; 50° C., 30 sec, 72° C., 1 min; and 1 cycle of: 72° C., 10 min. These techniques are well known in the art.

Control primer sets (which are designed to specifically amplify a 764-bp fragment for a single copy gene BDNF (brain derived neurotrophic factor)) were used as provided by the manufacture as positive control.

All PCR products were sequenced using an ABI (Foster, Cal.) automated DNA sequencer and an ABI 3700 DNA analyzer, and a 2.8 kb gene was assembled with ORF (open reading frame).

Example 3

Subcloning of Rat KCNQ5

For the full-length subcloning, the N- and C-terminus fragments with 462 bp overlap, which contains a unique NheI site, were generated separately. The fragments are truncated N- and C-terminal of rKCNQ5.

For the amplification of the GO-rich N-terminus, ADVANTAGE® GC2 PCR kit (Clontech, Palo Alto, Calif.) was used as directed by the manufacture. Mix 10 µl 5×GC2 PCR buffer, 5 µl GC melt, 500 ng DNA template, 2 µl of primer mix (10 µM each), 1 µl of 50×dNTP mix (10 mM each), 1 µl 50×ADVANTAGE® GC 1 Polymerase mix, and water to a total of 50 µl. PCR was done on DNA thermocycler 9600 for 30 cycles of: 95° C. 30 sec; 65° C., 2 min; and 68° C., 2 min. These techniques are well known in the art.

The primers used for the N-terminus PCR are as follows: GCCATGCCCCGCCACCACGC (forward primer; SEQ ID NO:7), AGGGCCTGAAGCGGGTTCGGTCGTT (reverse primer; SEQ ID NO:8). Primers were synthesized in house. 1 μl of 10 μM primers was used.

The PCR product was cloned into pcDNA-CTGFP-TOPO cloning vector, which contains the NheI site at the 3' of multi-cloning site. The TOPO vector and One shot TOPO cloning kit were purchased from Invitrogen. Briefly, 4 μl of PCR product was mixed with 1 μl of the TOPO vector, and incubated on ice for 5 min. Take 2 μl of the mixture and add into a vial of one shot TOP10 chemically competent E. coli and mix gently. Incubate on ice for 5 min. Heat shock the cells for 30 seconds at 42° C. Immediately transfer the tubes to ice. Add 250 μl of room temperature SOC medium. Cap the tube tightly and shake the tube horizontally (200 rpm) at 37° C. for 1 hr. Spread 100 μl from transformation on a prewarmed selective plate and incubate overnight at 37° C. The next day, colonies were pick and inoculated in a 2 ml LB culture for overnight, and plasmid prep was done on the automated QIAGEN plasmid prep station. These techniques are well known in the art.

One-step RT-PCR kit (Invitrogen) was used for the generation of the C-terminus fragment, and the PCR product was cloned into pcDNA-NTGFP-TOPO cloning vector, which contains NheI site at the 5' of the multi-cloning site. The primers used for the C-terminus PCR were: GGCTGGGAA-GATTGTCTCT (forward primer; SEQ ID NO:9), CGCTTA-GAAAGGAAACAAAGAAC (reverse primer; SEQ ID NO:10), Sequence No. 10. All the primers were made in house using 1 μl of 10 μM for the PCR reaction.

Both plasmids were digested with NheI. To do so, mix 1 μg of DNA, 1 μl of 10× reaction buffer, 1 μl of 10×BSA, 1 μl of Nhe, and water to a total of 10 μl. Incubate at 37° C. for 1 hr., and the NheI fragments containing the C-terminus of rKCNQ5 from pcDNA-NTGFP was purified. After digestion, electrophoresis was performed to separate the digested fragment in 1% agarose gel. The desired fragment was cut out and froze for 10 min, and then was spun for 10 min in a spin column (Freeze & Squeeze DNA gel extraction spin column, Biorad). The solution was collected and ligated to NheI digested pcDNA-CTGFP vector containing the N-terminus to generate a full-length rKCNQ5 cDNA in pcDNA-CTGFP vector. Ligation reaction (1 μl of 10× ligation buffer, 1 μl of ligase, 2 μl vector, 4 μl insert DNA, and 2 μl water) was done at room temperature overnight using T4 DNA ligase (Promega, Madison, W is., as directed by the manufacture). Ligation reaction was transformed into E. coli DH5a, and colonies were selected for plasmid preparation. Plasmids were digested with BamHI to ensure proper orientation.

Example 4

Functional Expression of Rat KCNQ5 in *Xenopus laevis* Oocytes

For Examples 4 and 5, the cRNAs of rKONQ5 were injected directly into Xenopus laevis oocytes and the electrophysiological recordings were performed 48-72 hours after RNA injection using two-electrode voltage clamp recording (see Jow F and Wang K-W, Mol. Brain Res. 80:269-78 (2000) for methods). The electrodes were filled with 3 M KCI solution with resistances ranging from 0.5 to 1.5 MΩ. The bath solution pf pH 7.4 was a "ND96" containing the following (in mM): NaCl, 96; KCl, 2; $CaCl_2$ 1.8; $MgCl_2$ 1; HEPES, 10 (see FIG. 1A). As shown in FIG. 1B, KCNQ5 current is sensitive to both standard KCNQ enhancing agent retigabine and a KCNQ selective blocker XE991. In other words, retigabine increased the channel current amplitude whereas XE991 decreased the current amplitude.

Example 5

Figure 2:
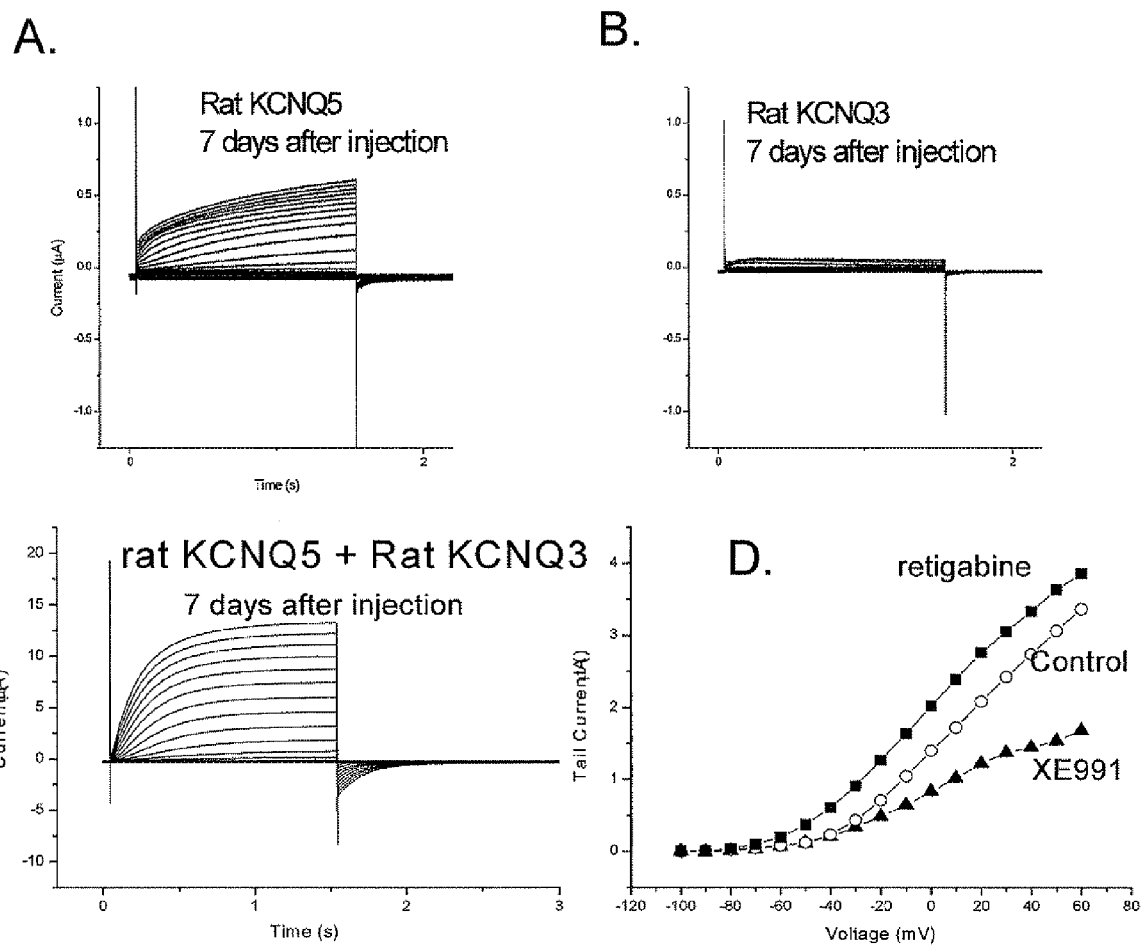
FIG. 2 shows that this rKCNQ5 subunit can form heteromeric ion channels when co-expressed with KCNQ3. There is a significant increase in the current amplitude of the rat KCNQ5/KCNQ3 heteromeric channels compared with that of the rKCNQ5 or rat KCNQ3 homomeric channels. The homomeric channels here refer to those with only one type of channel subunits expressed in Xenopus laevis oocytes. In this case, it refers to either rKCNQ5 alone (FIG. 2A) or rat KCNQ3 alone (FIG. 2B). Heteromeric channels means that the functional channels are composed of subunits of both rKCNQ5 and rat KCNQ3 (FIG. 2C). It is believed that those functional channels are composed of 4 such subunits. Therefore, the functional channels are "tetramers". If the 4 subunits are the same type (e.g. 4 rKCNQ5 subunits, or 4 rat KCNQ3 subunits), there are known as "homotetramers". If the 4 subunits in these functional channels are different (e.g., 2 rKCNQ5+2 rat KCNQ3, or 3 rat KCNQ5+1 rat KCNQ3, etc.), they are known as "heterotetramers". As also shown in FIG. 2D the current amplitudes of these heterotetramer channels are also increased by the KCNQ-enhancing agent retigabine and decrease by a KCNQ channel blocker XE991.

FIG. 2 shows that this rKCNQ5 subunit can form heteromeric ion channels when co-expressed with KCNQ3. There is a significant increase in the current amplitude of the rat KCNQ5/KCNQ3 heteromeric channels (FIG. 2C) compared with that of the rKCNQ5 (FIG. 2A) or rat KCNQ3 (FIG. 2B) homomeric channela As also shown in FIG. 2D, the current amplitudes of these heterotetramer channels are also increased by the KONO-enhancing agent retigabine and decrease by a KCNQ channel blocker XE991.

What is claimed is:

1. An isolated polypeptide comprising a KCNQ5 alpha subunit of a potassium channel, wherein the polypeptide:
   (i) has at least 99% sequence identity to the amino acid sequence of SEQ ID NO:2; and
   (ii) is capable of forming, with at least one additional KCNQ alpha subunit, a KCNQ potassium channel having the characteristic of voltage-gating.

2. A fusion protein comprising a first polypeptide consisting of the isolated polypeptide of claim 1 operably linked to a second, non-rKCNQ5 polypeptide.

3. A KCNQ dimeric channel comprising at least one KCNQ5 subunit which is the isolated polypeptide of claim 1.

4. The KCNQ dimeric channel of claim 3, wherein both channel subunits are the isolated polypeptide of claim 1.

5. The KCNQ dimeric channel of claim 3, wherein one subunit is KCNQ3.

6. The KCNQ dimeric channel of claim 5, wherein the KCNQ3 subunit is human KCNQ3.

7. A KCNQ tetrameric channel comprising at least one KCNQ5 subunit which is the isolated polypeptide of claim 1.

8. A KCNQ tetrameric channel wherein at least two of the four channel subunits are the isolated polypeptide of claim 1.

9. A KCNQ tetrameric channel wherein at least three of the four channel subunits are the isolated polypeptide of claim 1.

10. A KCNQ tetrameric channel, wherein all four of the channel subunits are the isolated polypeptide of claim 1.

11. The KCNQ tetrameric channel of claim 7, wherein at least one subunit is KCNQ3.

12. The KCNQ tetrameric channel of claim 11, wherein the KCNQ3 subunit is human KCNQ3.

13. The isolated polypeptide of claim 1, wherein the polypeptide comprises SEQ ID NO:2.

* * * * *